(12) United States Patent
Wacnik

(10) Patent No.: US 8,751,009 B2
(45) Date of Patent: Jun. 10, 2014

(54) TECHNIQUES FOR CONFIRMING A VOLUME OF EFFECT OF SUB-PERCEPTION THRESHOLD STIMULATION THERAPY

(71) Applicant: Medtronic, Inc., Minneapolis, MN (US)

(72) Inventor: Paul W. Wacnik, Brookline, MA (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 13/826,919

(22) Filed: Mar. 14, 2013

(65) Prior Publication Data
US 2013/0282078 A1    Oct. 24, 2013

Related U.S. Application Data

(60) Provisional application No. 61/637,653, filed on Apr. 24, 2012.

(51) Int. Cl.
*A61N 1/36* (2006.01)

(52) U.S. Cl.
USPC .......................................................... 607/59

(58) Field of Classification Search
CPC . A61N 1/3602; A61N 1/0551; A61N 1/3605; A61N 1/36067; A61N 1/36071
USPC ..................................... 607/46, 59
See application file for complete search history.

(56) References Cited

U.S. PATENT DOCUMENTS

| | | | |
|---|---|---|---|
| 6,587,724 B2 | 7/2003 | Mann | |
| 6,622,048 B1 | 9/2003 | Mann et al. | |
| 6,731,986 B2 | 5/2004 | Mann | |
| 7,082,333 B1 | 7/2006 | Bauhahn et al. | |
| 7,216,000 B2 | 5/2007 | Sieracki et al. | |
| 7,386,348 B2 | 6/2008 | North et al. | |
| 7,561,918 B2 | 7/2009 | Armstrong et al. | |
| 7,933,655 B2 | 4/2011 | Sieracki et al. | |
| 2006/0173495 A1 | 8/2006 | Armstrong et al. | |
| 2006/0241720 A1 | 10/2006 | Woods et al. | |
| 2007/0021801 A1 | 1/2007 | Heruth et al. | |
| 2007/0021802 A1 | 1/2007 | Heruth et al. | |
| 2007/0039625 A1 | 2/2007 | Heruth et al. | |
| 2007/0043392 A1 | 2/2007 | Gliner et al. | |
| 2007/0073356 A1 | 3/2007 | Rooney et al. | |

OTHER PUBLICATIONS

De Ridder et al., "Burst Spinal cord Stimulation: Toward Parasthesia-Free Pain Suppression," Neurosurgery, www.neurosurgery-online.com, vol. 66, No. 5, May 2010, pp. 986-990.
Van Buyten et al., "High-Frequency Spinal Cord Stimulation for the Treatment of Chronic Back Pain Patients: Results of a Prospective Multicenter European Clinical Study," Neuromodulation, www.neuromodulationjournal.com, Nov. 30, 2012, 7 pp.
De Ridder et al., "Burst spinal cord stimulation for limb and back pain," World Neurosugery, DOI: 10.1016/j.wneu.2013.01.040, Jan. 14, 2013, 32 pp.

*Primary Examiner* — Carl H Layno
*Assistant Examiner* — Paula J Stice
(74) *Attorney, Agent, or Firm* — Shumaker & Sieffert, P.A.

(57) ABSTRACT

A system may include a therapy delivery module configured to deliver electrical stimulation therapy to a tissue of a patient in accordance with a first stimulation therapy program. The first stimulation therapy program may define a first stimulation intensity below a perception threshold stimulation intensity of the patient. The therapy delivery module also may be configured to deliver electrical stimulation therapy to the tissue of the patient in accordance with a second stimulation therapy program. The second stimulation therapy program may define a second stimulation intensity at or above the perception threshold stimulation intensity. The system also may include a processor configured to determine stimulation parameter values for the first stimulation therapy program that result in a first volume of effect and determine stimulation parameter values for the second stimulation therapy program that result in a second volume of effect substantially the same as the first volume of effect.

26 Claims, 8 Drawing Sheets

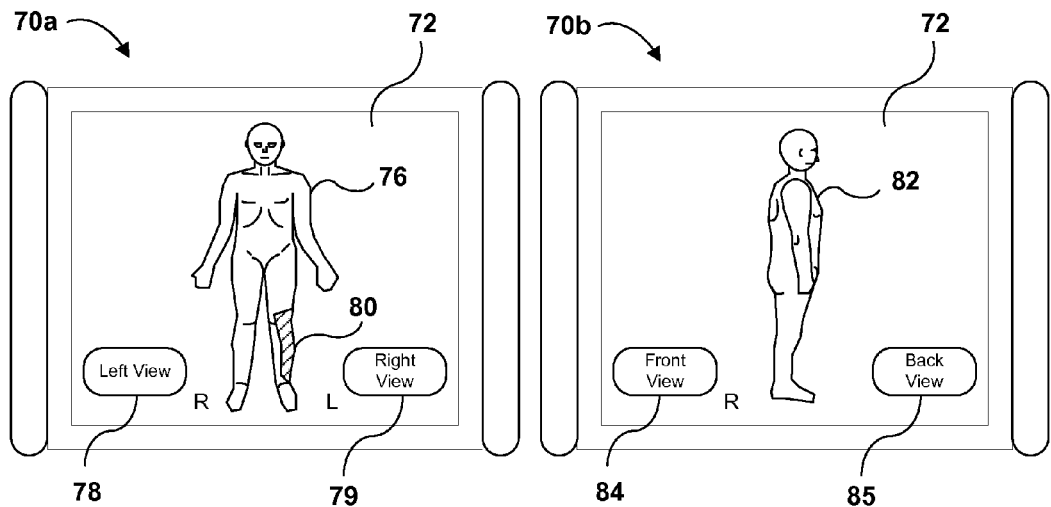
FIG. 6A
FIG. 6B
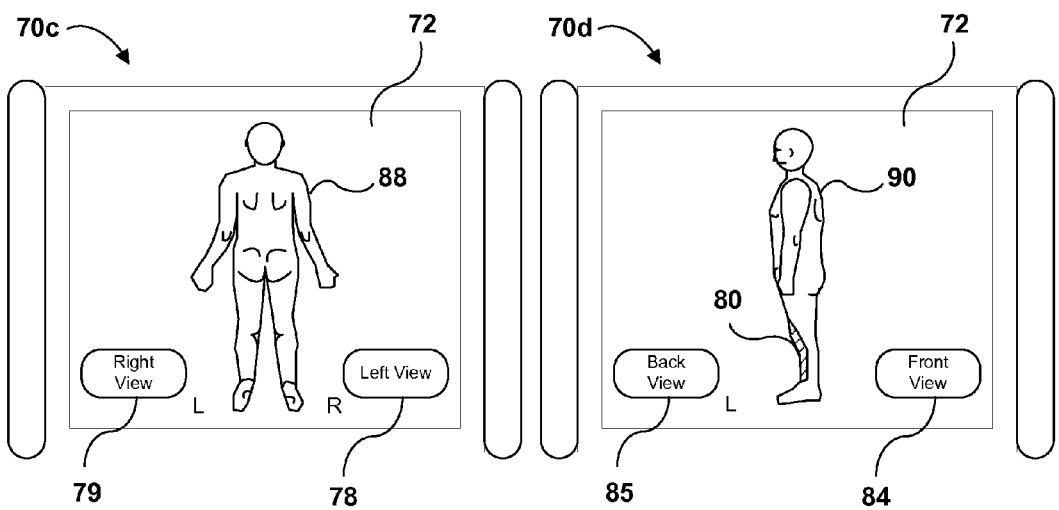
FIG. 6C
FIG. 6D

TECHNIQUES FOR CONFIRMING A VOLUME OF EFFECT OF SUB-PERCEPTION THRESHOLD STIMULATION THERAPY

This application claims the benefit of U.S. Provisional Patent Application Ser. No. 61/637,653 by Wacnik, which was filed on Apr. 24, 2012, and is entitled "TECHNIQUES FOR CONFIRMING A VOLUME OF EFFECT OF SUB-PERCEPTION THRESHOLD STIMULATION THERAPY." U.S. Provisional Patent Application Ser. No. 61/637,653 by Wacnik is incorporated herein by reference in its entirety.

TECHNICAL FIELD

The disclosure is directed to techniques for programming a medical device.

BACKGROUND

Medical devices, including implantable medical devices (IMDs), may be used to treat a variety of medical conditions. Medical electrical stimulation devices, for example, may deliver electrical stimulation therapy to a patient via external or implanted electrodes. Electrical stimulation therapy may include stimulation of nerve, muscle, the brain, or other tissue within a patient. In some examples, an electrical stimulation device is fully implanted within the patient. For example, an implantable electrical stimulation device may include an implantable electrical stimulation generator and one or more implantable leads carrying electrodes. Alternatively, the electrical stimulation device may comprise a leadless stimulator. In some cases, implantable electrodes may be coupled to an external electrical stimulation generator via one or more percutaneous leads or fully implanted leads.

Medical electrical stimulators have been proposed for use to relieve a variety of symptoms or conditions such as chronic pain, tremor, Parkinson's disease, depression, epilepsy, migraines, urinary or fecal incontinence, pelvic pain, sexual dysfunction, obesity, and gastroparesis. An electrical stimulator may be configured to deliver electrical stimulation therapy via leads that include electrodes implantable proximate to the spinal cord, pelvic nerves, gastrointestinal organs, peripheral nerves, or within the brain of a patient. Stimulation proximate the spinal cord, within the brain, and proximate peripheral nerves are often referred to as spinal cord stimulation (SCS) deep brain stimulation (DBS), and peripheral nerve stimulation (PNS), respectively.

SUMMARY

This disclosure describes systems and devices configured to deliver electrical stimulation therapy to a patient at an intensity below a perception threshold stimulation intensity of the patient, and methods for delivering the sub-perception threshold stimulation. A perception threshold stimulation intensity may be a minimum stimulation intensity at which a patient substantially perceives the electrical stimulation therapy. When an IMD delivers electrical stimulation therapy to a patient at an intensity below the perception threshold stimulation intensity, the patient may not perceive a substantial effect of the delivery of the stimulation therapy.

In accordance with some aspects of this disclosure, an approximate volume of effect of the sub-perception threshold electrical stimulation therapy (the first stimulation therapy) may be determined. The approximate volume of effect of the sub-perception threshold stimulation therapy may represent the volume of tissue in which the sub-perception threshold stimulation therapy produces a therapeutic effect, even though the patient may not substantially perceive the therapeutic effect. The approximate volume of effect of the sub-perception threshold stimulation therapy may be used in a technique for confirming that the selected electrical stimulation parameter values are appropriate for delivering electrical stimulation therapy to a desired tissue volume. In some examples, the approximate volume of effect of the sub-perception threshold stimulation therapy may be determined theoretically, e.g., using at least one mathematical model. In other examples, the approximate volume of effect may be determined experimentally, e.g., by delivering electrical stimulation therapy at approximately the perception threshold stimulation intensity (e.g., slightly above the perception threshold stimulation intensity) and receiving an indication from the patient indicating the volume of effect of the stimulation therapy. The intensity of the stimulation therapy may then be reduced below the perception threshold stimulation intensity for use in delivering the first stimulation therapy.

Additionally, in some examples, a volume of effect for a second stimulation therapy delivered with a stimulation intensity at or above the perception threshold stimulation intensity may be determined. Similar to the volume of effect for the first stimulation therapy, the volume of effect for the second stimulation therapy may be determined theoretically or experimentally. The volume of effect of the second stimulation therapy may represent the volume of tissue in which the second stimulation therapy produces an effect that is perceivable to the patient, e.g., paresthesia. The stimulation parameter values according to which the first and second stimulation therapies are delivered may be selected so the volume of effect of the second stimulation therapy is substantially the same (e.g., the same or nearly the same) as the volume of effect of the first stimulation therapy. Additionally, the location within the patient of the volume of effect of the second stimulation therapy may be substantially the same (e.g., the same or nearly the same) as the volume of effect of the first stimulation therapy.

In this way, delivery of the second stimulation therapy, of which the patient can perceive, may be used to approximate the volume of effect of the first stimulation therapy. The patient or another user, such as a clinician, may utilize the correspondence between the volume of effect of the second stimulation therapy and the volume of effect of the first stimulation therapy to confirm the location at which the first stimulation therapy is being delivered, e.g., by instructing the IMD to temporarily deliver the second stimulation therapy.

In one example, the disclosure is directed to a system that includes a therapy delivery module configured to deliver electrical stimulation therapy to a tissue of a patient in accordance with a first stimulation therapy program. The first stimulation therapy program may define a first stimulation intensity below a perception threshold stimulation intensity of the patient. The therapy delivery module also may be configured to deliver stimulation therapy to the tissue of the patient in accordance with a second stimulation therapy program. The second stimulation therapy program may define a second stimulation intensity at or above the perception threshold stimulation intensity. In accordance with this example, the system also includes a processor configured to determine stimulation parameter values for the second stimulation therapy program that result in a second volume of effect within the patient and determine stimulation parameter values for the first stimulation therapy program that result in a first volume of effect within the patient that is substantially the same as the second volume of effect.

In another example, the disclosure is directed to a method that includes delivering, by a therapy delivery module, electrical stimulation therapy to a tissue of a patient in accordance with a first stimulation therapy program, where the first stimulation therapy program defines a first stimulation intensity below a perception threshold stimulation intensity of the patient. The method also may include delivering, by the therapy delivery module, stimulation therapy to the tissue of the patient in accordance with a second stimulation therapy program, where the second stimulation therapy program defines a second stimulation intensity at or above the perception threshold stimulation intensity. In accordance with this example, the method also includes determining, by a processor, stimulation parameter values for the second stimulation therapy program that result in a second volume of effect within the patient. The method further may include determining, by the processor, stimulation parameter values for the first stimulation therapy program that result in a first volume of effect within the patient that is substantially the same as the second volume of effect.

In an additional example, the disclosure is directed to a system that includes means for delivering electrical stimulation therapy to a tissue of a patient in accordance with a first stimulation therapy program, where the first stimulation therapy program defines a first stimulation intensity below a perception threshold stimulation intensity of the patient. The system also may include means for delivering stimulation therapy to the tissue of the patient in accordance with a second stimulation therapy program, where the second stimulation therapy program defines a second stimulation intensity at or above the perception threshold stimulation intensity. In accordance with this example, the system also includes means for determining stimulation parameter values for the second stimulation therapy program that result in a second volume of effect within the patient, and means for determining stimulation parameter values for the first stimulation therapy program that result in a first volume of effect within the patient that is substantially the same as the second volume of effect.

In another example, the disclosure is directed to a computer-readable storage medium that includes instructions that, when executed by at least one processor, cause the at least one processor to control a therapy delivery module to deliver electrical stimulation therapy to a tissue of a patient in accordance with a first stimulation therapy program, where the first stimulation therapy program defines a first stimulation intensity below a perception threshold stimulation intensity of the patient. The instructions also may cause the at least one processor to control the therapy delivery module to deliver stimulation therapy to the tissue of the patient in accordance with a second stimulation therapy program, wherein the second stimulation therapy program defines a second stimulation intensity at or above the perception threshold stimulation intensity. Further, the instructions may cause the at least one processor to determine stimulation parameter values for the second stimulation therapy program that result in a second volume of effect within the patient and determine stimulation parameter values for the first stimulation therapy program that result in first volume of effect within the patient that is substantially the same as the second volume of effect.

In a further example, the disclosure is directed to an IMD that includes a therapy delivery module and a processor. In accordance with this example, the processor is configured to control the therapy delivery module to deliver electrical stimulation therapy to a patient in accordance with the first stimulation therapy program. The first stimulation therapy program may define a first stimulation intensity below a perception threshold stimulation intensity of the patient and produce a first volume of effect within the patient. The processor also may be configured to receive a signal indicating an instruction from a user to switch therapy delivery from the first stimulation therapy program to a second stimulation therapy program. The second stimulation therapy program may define a second stimulation intensity at or above the perception threshold stimulation intensity and produce a second volume of effect within the patient that is substantially the same as the first volume of effect. Further, the processor may be configured to, in response to reception of the signal, control the therapy delivery module to deliver electrical stimulation therapy to the patient in accordance with the second stimulation therapy program to confirm the first volume of effect of the first stimulation therapy program.

In an additional example, the disclosure is directed to a method that includes delivering, by a therapy delivery module, electrical stimulation therapy to a patient in accordance with the first stimulation therapy program. The first stimulation therapy program may define a first stimulation intensity below a perception threshold stimulation intensity of the patient and produce a first volume of effect within the patient. The method also may include receiving, by a processor, a signal indicating an instruction from a user to switch therapy delivery from the first stimulation therapy program to a second stimulation therapy program. The second stimulation therapy program may define a second stimulation intensity at or above the perception threshold stimulation intensity and produce a second volume of effect within the patient that is substantially the same as the first volume of effect. Additionally, the method may include, in response to receiving the signal, delivering, by the therapy delivery module, electrical stimulation therapy to the patient in accordance with the second stimulation therapy program to confirm the first volume of effect of the first stimulation therapy program.

In a further example, the disclosure is directed to a system that includes means for delivering electrical stimulation therapy to a patient in accordance with the first stimulation therapy program. The first stimulation therapy program may define a first stimulation intensity below a perception threshold stimulation intensity of the patient and produce a first volume of effect within the patient. In accordance with this example, the system also includes means for receiving a signal indicating an instruction from a user to switch therapy delivery from the first stimulation therapy program to a second stimulation therapy program. The second stimulation therapy program may define a second stimulation intensity at or above the perception threshold stimulation intensity and produce a second volume of effect within the patient that is substantially the same as the first volume of effect. Further, the system may include means for, in response to receiving the signal, delivering electrical stimulation therapy to the patient in accordance with the second stimulation therapy program to confirm the first volume of effect of the first stimulation therapy program.

In another example, the disclosure is directed to a computer-readable storage medium comprising instructions that cause at least one processor to control a therapy delivery module to deliver electrical stimulation therapy to a patient in accordance with the first stimulation therapy program. The first stimulation therapy program may define a first stimulation intensity below a perception threshold stimulation intensity of the patient and produce a first volume of effect within the patient. The instructions also may cause the at least one processor to receive a signal indicating an instruction from a user to switch therapy delivery from the first stimulation therapy program to a second stimulation therapy program. The second stimulation therapy program may define a second stimulation intensity at or above the perception threshold stimulation intensity and produce a second volume of effect within the patient that is substantially the same as the first volume of effect. Additionally, the instruction may cause the at least one processor to, in response to receiving the signal, control the therapy delivery module to deliver stimulation therapy to the patient in accordance with the second stimulation therapy program to confirm the first volume of effect of the first stimulation therapy program.

The details of one or more examples are set forth in the accompanying drawings and the description below. Other features, objects, and advantages will be apparent from the description and drawings, and from the claims.

BRIEF DESCRIPTION OF DRAWINGS

FIGS. 6A-6D are example user interface screens that may be presented to a user by an external programmer to allow the user to input a pain region and/or a volume of effect of a stimulation therapy.

DETAILED DESCRIPTION

Figure 1:
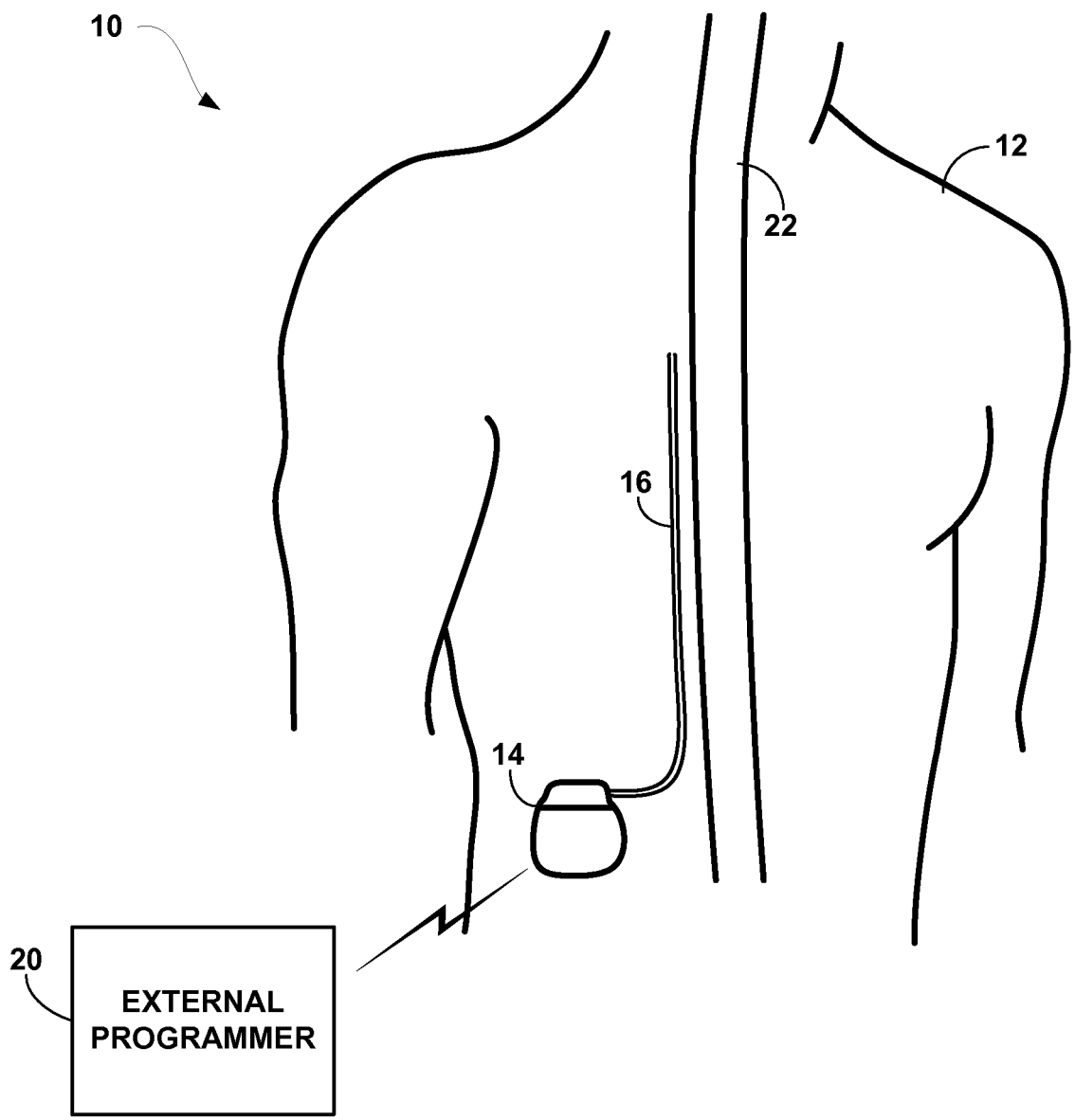
FIG. 1 is a conceptual diagram illustrating an example system that includes an IMD configured to deliver spinal cord stimulation (SCS) therapy.

This disclosure describes systems and devices configured to deliver electrical stimulation therapy at an intensity below a perception threshold stimulation intensity to a patient, and methods for delivering the electrical stimulation therapy to the patient. The electrical stimulation therapy may provide relief from chronic pain by preventing transmission of pain signals through the stimulated nerves. In some examples, an IMD may deliver electrical stimulation therapy at a first location (e.g., the spinal cord) to relieve pain that the patient perceives originating from a second location (e.g., lower back and/or legs) that is different from the first location (e.g., in SCS). In other examples, an IMD may deliver electrical stimulation therapy at a location at which the patient perceives pain (e.g., in PNS).

In some cases, the IMD may deliver electrical stimulation therapy in such a way that the patient does not substantially perceive the delivery of the electrical stimulation therapy, other than the total or partial absence of the chronic pain being addressed. Such an electrical stimulation therapy is described herein as defining an intensity below a perception threshold stimulation intensity. While this would be a good patient outcome, it may be difficult to define stimulation parameters that provide efficacious therapy while consuming a low amount of energy when the therapy is delivered below the perception threshold of the patient. For example, the IMD may deliver the electrical stimulation therapy to a much larger area than is necessary to cover the chronic pain the patient perceives from the second area, thereby unnecessarily draining the battery.

In many cases, clinicians may implant within a patient a greater number of electrodes than is needed to deliver electrical stimulation therapy at a particular time. The greater number of electrodes allows the clinician to flexibly and adaptably define stimulation programs that stimulate different areas of the spinal cord, e.g., areas that correspond to the different areas from which the patient perceives chronic pain. As such, a clinician may work with a patient in a process of mapping the volume of effect of the electrical stimulation therapy and the area of chronic pain. Such mapping may include stimulating different areas of the spinal cord by changing which electrodes are used for stimulation (the electrode configuration) and/or by changing one or more energy parameters of the stimulation (e.g., voltage or current amplitude, pulse frequency, pulse width, duty cycle, or the like). Together, the electrode configuration and other stimulation parameters may define a stimulation therapy program. The patient may report which of the different stimulation therapy programs most effectively alleviates the patient's chronic pain. A preferred stimulation therapy program defining the stimulation parameters and stimulation electrode(s) that produced a therapeutic effect preferred by the patient can then be set in the IMD for chronic delivery of therapy.

Some patients may prefer therapeutic stimulation for chronic pain that is imperceptible (e.g., other than a reduction in chronic pain). However, mapping the coverage of the stimulation therapy can be difficult if the stimulation therapy is delivered below the perception threshold of the patient. While a patient may feel changes in pain relief from the electrical stimulation therapy during a mapping process, the true volume of effect of the electrical stimulation therapy may remain unknown. As mentioned above, this can lead to unnecessary stimulation and energy expenditure, among other things.

The present disclosure describes, among other things, a stimulation system having a therapy mode and a mapping mode. In the therapy mode, the stimulation system is configured to deliver electrical stimulation therapy with a stimulation intensity below a perception threshold stimulation intensity. As described below, the perception threshold stimulation intensity may be a minimum stimulation intensity at which a patient substantially perceives the electrical stimulation therapy (e.g., the patient subjectively identifies the perceived effect as substantial). In the mapping mode, the stimulation system is configured to deliver electrical stimulation therapy at or above the perception threshold stimulation intensity to allow the patient to understand or determine what location(s) (referred to herein as volume(s) of effect) are covered by the sub-perception threshold stimulation therapy. In some examples, the stimulation system may deliver the sub-perception threshold stimulation therapy to a first location of the patient (e.g., an area of the spinal cord) and the stimulation therapy may affect a second location of the patient (e.g., back, legs). In other examples, the stimulation system may deliver the sub-perception threshold stimulation therapy to a first location of the patient (e.g., a location proximate to a peripheral nerve) and the stimulation therapy may affect the first location.

When a stimulation therapy program is identified that provides coverage suitable to the patient and defines a stimulation intensity above the perception threshold stimulation intensity, a therapy mode can be entered (e.g., based on an input to an external programmer by a user), where the stimulation intensity is automatically changed to be below the perception threshold of the patient while substantially maintaining the coverage (e.g., volume of effect) of the stimulation therapy program identified in the mapping mode. If adjustment or confirmation of the coverage of the electrical stimulation therapy is later desired, the mapping program can be entered (e.g., automatically based on a schedule or based on an input to an external programmer by a user), which automatically changes the stimulation intensity to be above the perception threshold stimulation intensity of the patient while substantially maintaining the area of stimulation therapy coverage (e.g., the volume of effect of the electrical stimulation therapy).

The user may not manually change the stimulation output to be above or below the perception threshold stimulation intensity of the patient (e.g., by manually changing the stimulation amplitude, pulse width, or frequency) when using such a system. Rather, the change in the stimulation intensity to be above or below the perception threshold is automatically made by the IMD and/or the external programmer in response to receiving an indication of user input switching between the mapping and therapy modes. In some cases, the same one or more electrodes selected based on preferred coverage out of a plurality of implanted electrodes can be used for stimulation in both of the mapping and therapy modes. For example, the same distribution ratio of stimulation energy can be used between electrodes to provide the same stimulation coverage when switching between the mapping and therapy modes An intensity of electrical stimulation may be a function of one or more stimulation parameter values, such as current of voltage pulse amplitude, pulse rate, and pulse width in the case of electrical pulses. A perception threshold stimulation intensity may be a minimum stimulation intensity at which a patient substantially perceives the electrical stimulation therapy (e.g., the patient subjectively identifies the perceived effect as substantial). For example, the perception threshold stimulation intensity may be defined as the stimulation intensity at which the patient first perceives (e.g., feels) one or more substantial effects from the electrical stimulation therapy, such as an acute, physiologically significant response, when increasing the stimulation intensity from a low intensity to a higher intensity. The acute, physiologically significant response may include, for example, a motor response, a stimulation perception response, or a detected physiological response, such as a nerve action potential. Hence, in some examples, the patient may perceive an effect of the electrical stimulation therapy that is delivered at an intensity less than the perception threshold stimulation intensity, but the patient may define the perceived effect as not being substantial. For example, the patient may perceive some paresthesia due to the sub-perception threshold stimulation therapy, but may identify the paresthesia as not being substantial. The perceived effect of the sub-threshold stimulation therapy may be substantially diminished or substantially absent compared to a perceived effect of a supra-threshold stimulation therapy (e.g., an electrical stimulation therapy delivered at a stimulation intensity above the perception threshold stimulation intensity).

A stimulation perception response may be observed and reported by the patient, e.g., as paresthesia or another sensation. A motor response or a physiological response (e.g., a nerve impulse or non-therapeutic effect) may be reported by the patient, observed by a clinician, or automatically detected by one or more sensors internal or external to the patient. In some examples, whether a response is physiologically significant may be defined by the patient or the clinician. For example, the stimulation may elicit movement of a toe of the patient, and the patient or clinician may define the movement of the toe as physiologically significant when the movement of the toe is perceptible or when the movement of the toe is above some arbitrary amount defined by the patient or the clinician. The physiological response may or may not be a therapeutic response. For example, a therapeutic response may be paresthesia, and a non-therapeutic response may be activation of a muscle fiber, which may cause the muscle fiber to contract. In some examples, an acute response may be defined as a physiological response that occurs within about 30 seconds or less (e.g., about 10 seconds) of the patient receiving the stimulation (e.g., the initiation of the stimulation at the particular intensity level). One example of a technique that may be used to determine a perception threshold stimulation therapy for a particular patient is described below with reference to FIG. 7.

When an IMD delivers electrical stimulation therapy to the patient at an intensity below the perception threshold stimulation intensity of the patient, the patient may not perceive the delivery of the stimulation therapy. In some examples, the patient or a clinician supervising the electrical stimulation therapy may desire to confirm that the sub-perception threshold electrical stimulation therapy is resulting in delivery of therapy to a desired tissue volume. The desired tissue volume may be, for example, a tissue volume in which the patient experiences pain, or a tissue volume proximate a spinal cord of the patient, where nerves that enervate a pain site of the patient connect to the spinal cord. For electrical stimulation therapies delivered to treat therapies other than pain, the desired tissue volume may be determined based on the therapy delivery site and the desired therapeutic effect.

In accordance with some aspects of this disclosure, an approximate volume of effect of the sub-perception threshold stimulation therapy (the first stimulation therapy) may be determined. The approximate volume of effect of the sub-perception threshold stimulation therapy may represent the volume of tissue in which the sub-perception threshold stimulation therapy produces a therapeutic effect, even though the patient may not perceive the therapeutic effect. In some examples, the approximate volume of effect of the first stimulation therapy may be determined theoretically, e.g., using at least one mathematical model. An example technique for theoretically determining the volume of effect of the first stimulation therapy is described below with respect to FIG. 10.

In other examples, the approximate volume of effect may be determined experimentally, e.g., by delivering electrical stimulation therapy at approximately the perception threshold stimulation intensity (e.g., slightly above the perception threshold stimulation intensity) and receiving an indication from the patient indicating the volume of effect of the stimulation therapy. The intensity of the stimulation therapy may then be reduced below the perception threshold stimulation intensity for use in delivering the first stimulation therapy. The volume of effect indicated by the patient for the stimulation therapy delivered at approximately the perception threshold stimulation intensity may be used as the approximate volume of effect for the first stimulation therapy. In other examples, the approximate volume of effect for the first stimulation therapy may be extrapolated based on volumes of effect of a set of supra-perception threshold stimulation intensities. Example techniques for determining the first volume of effect are described below with respect to FIGS. 7 and 8.

Additionally, a volume of effect for a second stimulation therapy delivered with an intensity at or above the perception threshold stimulation intensity may be determined. The second stimulation therapy may define a stimulation intensity that is greater than the perception threshold stimulation intensity. The volume of effect of the second stimulation therapy may represent the volume of tissue in which the second stimulation therapy produces an effect that the patient may perceive, e.g., paresthesia. Similar to the volume of effect for the first stimulation therapy, the volume of effect for the second stimulation therapy may be determined theoretically or experimentally. The stimulation parameter values according to which the second stimulation therapy is delivered may be selected so the volume of effect of the second stimulation therapy is substantially the same (e.g., the same or nearly the same) as the volume of effect of the first stimulation therapy and the location of the second volume of effect within a body of the patient is substantially the same as the location of the first volume of effect.

In this way, delivery of the second stimulation therapy, which the patient can perceive, may be used to approximate the volume of effect of the first stimulation therapy. The patient or another user, such as a clinician, may utilize the correspondence between the size and location of the volume of effect of the second stimulation therapy and the size and location of the volume of effect of the first stimulation therapy to confirm the location at which the first stimulation therapy is being delivered, e.g., by instructing the IMD to temporarily deliver the second stimulation therapy. In some cases, the IMD or an external programmer may be configured to switch between the first stimulation therapy and the second stimulation therapy based on a schedule. For example, the IMD may temporarily deliver the second stimulation therapy periodically, e.g., on an hourly, daily, or weekly basis, to allow the patient to temporarily perceive the effect of the second stimulation therapy and understand where the first stimulation therapy is affecting the patient. In other cases, the patient or another user may utilize an external programmer to input a command, which the programmer communicates to the IMD. The command may cause or control the IMD to temporarily deliver the second stimulation therapy. In some examples, the correspondence between the volumes of effect of the first and second stimulation therapies may be used to determine if the volume of effect of the first stimulation therapy continues to overlap a desired tissue volume, e.g., a tissue volume in which the patient experiences pain, or a tissue volume proximate a spinal cord of the patient at which nerves that enervate a pain site of the patient connect to the spinal cord.

Figure 2:
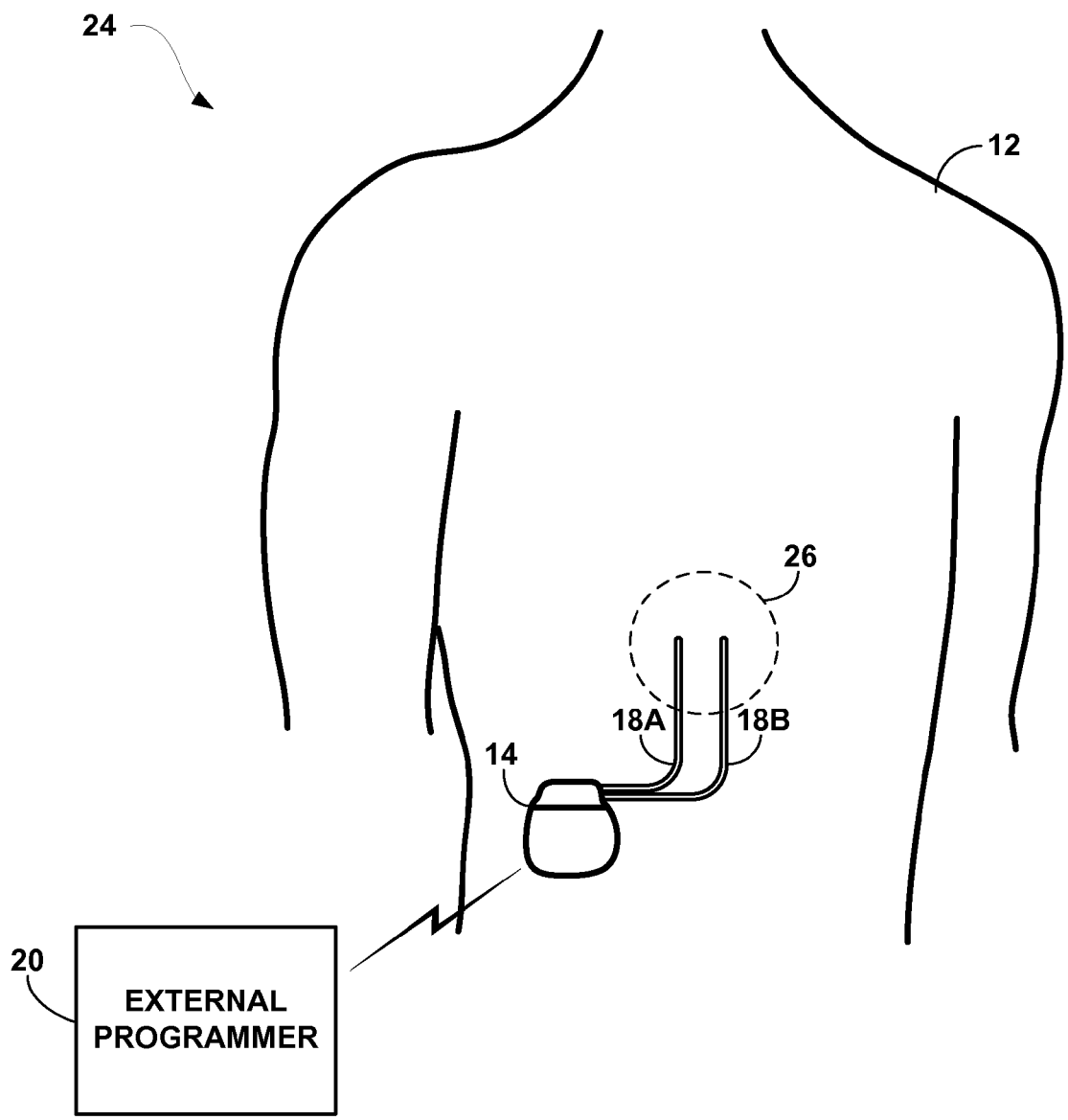
FIG. 2 is a conceptual diagram illustrating an example system that includes an IMD configured to deliver peripheral nerve stimulation (PNS) or peripheral nerve field stimulation (PNFS) therapy.

FIG. 1 is a conceptual diagram illustrating an example therapy system 10 that includes an implantable medical device (IMD) 14 configured to deliver spinal cord stimulation (SCS) therapy to patient 12. Although the techniques described in this disclosure are generally described with respect to pain management therapy for illustration, other types of therapy may incorporate one or more mapping techniques disclosed herein. In addition, FIG. 1 is directed to SCS therapy. However, therapy system 10 may alternatively be configured to provide PNS or PNFS, as shown in FIG. 2; occipital nerve stimulation; sacral nerve stimulation (SNS); pelvic floor stimulation; or any other electrical stimulation therapy.

As shown in FIG. 1, therapy system 10 includes an IMD 14 and external programmer 20. IMD 14 may be coupled to one or more lead 16. IMD 14 and lead 16 are shown implanted in a patient 12, who is ordinarily a human patient. In the example of FIG. 1, IMD 14 is an implantable electrical stimulator that delivers neurostimulation therapy to patient 12, e.g., for relief of chronic pain or other symptoms. IMD 14 may be a chronic electrical stimulator that remains implanted within patient 12 for weeks, months, or years. In the example of FIG. 1, IMD 14 and lead 16 may be used to deliver chronic SCS therapy. In other examples, IMD 14 may be a temporary, or trial, stimulator used to screen or evaluate the efficacy of electrical stimulation for chronic therapy. IMD 14 may be implanted in a subcutaneous tissue pocket, within one or more layers of muscle, or another internal location.

IMD 14 may be constructed of any polymer, metal, or composite material sufficient to house the components of IMD 14 (e.g., components illustrated in FIG. 3) within patient 12. In this example, IMD 14 may be constructed with a biocompatible housing, such as titanium or stainless steel, or a polymeric material such as silicone or polyurethane, and surgically implanted at a site in patient 12 near the pelvis, abdomen, or buttocks. The outer housing of IMD 14 may be configured to provide a hermetic seal for components.

IMD 14 may deliver electrical stimulation energy via lead 16 as a series of electrical pulses or a substantially continuous electrical waveform. In some examples, the electrical stimulation energy may be constant current or constant voltage pulses, which are delivered from IMD 14 to one or more targeted locations within patient 12 via one or more electrodes (not shown in FIG. 1) of lead 16. The parameters for a therapy program that controls delivery of stimulation energy by IMD 14 may include information identifying which electrodes have been selected for delivery of stimulation according to a stimulation program and the polarities of the selected electrodes, i.e., the electrode configuration for the program; voltage or current amplitude; pulse frequency (or pulse rate); pulse shape; pulse width; and/or duty cycle of stimulation delivered by the electrodes. In examples in which IMD 14 provides electrical stimulation in the form of a continuous waveform, the continuous waveform may be characterized by, for example, a current or voltage amplitude, a waveform frequency, a shape of the waveform, a duration of the waveform, or the like.

In the example of FIG. 1, lead 16 is implanted within patient 12. Lead 16 tunnels through tissue of patient 12 from along spinal cord 22 to a subcutaneous tissue pocket or other internal location where IMD 14 is implanted. Although lead 16 may be a single lead, lead 16 may include a lead extension or other segments that may aid in implantation or positioning of lead 16. In addition, a proximal end of lead 16 may include a connector (not shown) that electrically couples to a header of IMD 14, either directly or indirectly (e.g., via a lead extension). Although only one lead 16 is shown in FIG. 1, therapy system 10 may include two or more leads, each coupled to IMD 14 and directed to similar or different target tissue sites. For example, multiple leads may be disposed along spinal cord 22 or leads may be directed to spinal cord 22 and/or other locations within patient 12.

Lead 16 may carry one or more electrodes (not shown in FIG. 1) that are placed adjacent to the target tissue, e.g., spinal cord 22 for SCS therapy. One or more electrodes may be disposed at a distal tip of lead 16 and/or at other positions at intermediate points along lead 16, for example. Electrodes of lead 16 transfer electrical stimulation generated by an electrical stimulation generator in IMD 14 to tissue of patient 12. The electrodes may be electrode pads on a paddle lead, circular (e.g., ring) electrodes surrounding the body of the lead, conformable electrodes, cuff electrodes, segmented electrodes (e.g., electrodes disposed at different circumferential positions around the lead instead of a continuous ring electrode), or any other type of electrodes capable of forming unipolar, bipolar or multipolar electrode configurations for therapy. In general, ring electrodes arranged at different axial positions at the distal ends of lead 16 will be described for purposes of illustration.

Although lead 16 is described as generally delivering or transmitting electrical stimulation signals, lead 16 may additionally transmit electrical signals from patient 12 to IMD 14 for monitoring. For example, IMD 14 may utilize detected nerve impulses to diagnose the condition of patient 12 or adjust the delivered stimulation therapy. Lead 16 may thus transmit electrical signals to and/or from patient 12.

A user, such as a clinician or patient 12, may interact with a user interface of an external programmer 20 to program IMD 14. Programming of IMD 14 may refer generally to the generation and transfer of commands, programs, or other information to control the operation of IMD 14. In this manner, IMD 14 may receive the transferred commands and programs from programmer 20 to control stimulation therapy. For example, external programmer 20 may transmit programs, parameter adjustments, program selections, group selections, user input, or other information to control the operation of IMD 14, e.g., by wireless telemetry or wired connection.

In some cases, external programmer 20 may be characterized as a clinician (or physician) programmer if it is primarily intended for use by a clinician. In other cases, external programmer 20 may be characterized as a patient programmer if it is primarily intended for use by a patient. A patient programmer may be generally accessible to patient 12 and, in many cases, may be a portable device that may accompany patient 12 throughout the patient's daily routine. For example, a patient programmer may receive input from patient 12 when the patient wishes to terminate or change stimulation therapy when the stimulation is undesirable (e.g., uncomfortable). In general, a physician or clinician programmer may support selection and generation of programs by a clinician for use by IMD 14, whereas a patient programmer may support adjustment and selection of such programs by a patient during ordinary use. In other examples, external programmer 20 may be included in, or part of, an external charging device that recharges a power source of IMD 14. In this manner, a user may program and charge IMD 14 using one device or multiple devices.

Information may be transmitted between external programmer 20 and IMD 14. IMD 14 and programmer 20 may communicate via wireless communication using any techniques known in the art. An example communication technique includes, for example, radiofrequency (RF) telemetry, but other techniques are also contemplated. In some examples, programmer 20 may include a communication head that may be placed proximate to the patient's body near the IMD 14 implant site in order to improve the quality or security of communication between IMD 14 and programmer 20. Communication between programmer 20 and IMD 14 may occur during power transmission or separate from power transmission.

In accordance with one or more aspects of this disclosure, IMD 14 may be configured to deliver electrical stimulation therapy to patient 12 according to a first stimulation therapy program that defines a sub-perception threshold stimulation intensity. As described above, the perception threshold stimulation intensity may be defined as a minimum stimulation intensity at which patient 12 perceives a substantial effect of the stimulation therapy. In some examples, the substantial effect may be an acute, physiologically significant response. For example, the acute, physiologically significant response may be a motor response, a stimulation perception response, or a detected physiological response, such as a nerve action potential. The physiological response may or may not be a therapeutic response.

In some instances, stimulation therapy delivered below the perception threshold stimulation intensity may provide a therapeutic effect to patient 12, even though patient 12 does not perceive the delivery of the stimulation therapy. For example, sub-perception threshold stimulation intensity may be useful in treating pain or another condition or disease experienced by patient 12, e.g., may reduce pain experienced by patient 12.

However, because patient 12 does not substantially perceive the delivery of sub-perception threshold stimulation therapy (e.g., patient 12 may not perceive a substantial physiological effect from the stimulation therapy, such as paresthesia or a motor response), it may be difficult to determine the location at which the sub-perception threshold stimulation therapy is being delivered (e.g., the volume of tissue affected by the sub-perception threshold stimulation therapy), particularly if an area of pain experienced by patient 12 changes over time or electrodes carried by lead 16 move over time within patient 12. Because of this, patient 12 or a clinician supervising the electrical stimulation therapy may desire to confirm that the sub-perception threshold stimulation therapy is resulting in delivery of therapy to a desired tissue volume. The desired tissue volume may be, for example, a tissue volume proximate spinal cord 22 at which nerves that enervate a pain site of patient 12 connect to the spinal cord 22 or a tissue volume in which patient 12 experiences pain. In some examples, the desired tissue volume may be determined by the clinician, alone or with the aid of patient 12, based on the patient condition and the symptoms for which therapy system 10 is implemented to manage.

To facilitate determination of whether the sub-perception threshold stimulation therapy (a first stimulation therapy) is being delivered to a desired tissue volume, e.g., a tissue volume desired by patient 12 or a clinician supervising treatment of patient 12, an approximate volume of effect of the first stimulation therapy may be determined. The approximate volume of effect may be substantially equal to (e.g., equal to or nearly equal to) a volume of tissue affected by the first stimulation therapy, e.g., a volume of tissue in which the first stimulation therapy produces a therapeutic effect. The approximate volume of effect of the first stimulation therapy may be mapped to a volume of effect of a supra-perception threshold stimulation therapy (e.g., a second stimulation therapy, which has an intensity at or above the perception threshold stimulation intensity), such that the first volume of effect is substantially the same (e.g., the same or nearly the same) as the second volume of effect.

By mapping the approximate volume of effect of the first stimulation therapy to the volume of effect of second stimulation therapy, the second stimulation therapy subsequently may be invoked by patient 12 or another user to determine an approximate volume of tissue which the first stimulation therapy is affecting. This may be used to, for example, determine if the first stimulation therapy is affecting a volume of tissue that overlaps a region of pain experienced by patient 12.

As another example, delivery of the second stimulation therapy on a temporary basis may be used by patient 12 or another user to determine whether lead 16 has moved so the first stimulation therapy is no longer being directed to a desired volume of tissue.

In other examples, instead of the second stimulation therapy being invoked by a user, the IMD or an external programmer may be configured to switch between the first stimulation therapy and the second stimulation therapy based on a schedule. For example, the IMD may temporarily deliver the second stimulation therapy periodically, e.g., on an hourly, daily, or weekly basis, to allow the patient to temporarily perceive the effect of the second stimulation therapy and understand where the first stimulation therapy is affecting the patient.

As described above, the first and second volumes of effect may be determined theoretically, e.g., using one or more mathematical models, or experimentally, e.g., by delivering stimulation and receiving an indication from patient 12 of the volume of effect.

For example, IMD 14, external programmer 20, or another computing device may determine the approximate volume of effect using an algorithm that models the volume of effect based on a stimulation therapy program, an anatomy of patient 12, and the hardware characteristics of therapy system 10. In the case of therapy system 10 (FIG. 1), the hardware characteristics may include the type of IMD 14, which may include the energy threshold for the particular type of IMD 14, the type of lead 16, which may include the type of electrodes carried by lead 16 (e.g., ring electrodes, partial ring electrodes or segmented electrodes), and a baseline impedance presented to IMD 14 at the time of programming, i.e., the impedance of the entire path between IMD 14 and the target tissue site, including the lead conductors, electrodes, and patient tissue through which stimulation propagates. In examples in which a therapy system 10 includes two or more leads, the hardware characteristics of therapy system 10 may include a baseline distance between the electrodes of the respective leads. The baseline spacing between the electrodes of the leads may be, for example, the spacing between the electrodes at the time of implantation of the leads. The algorithm for generating the volume of effect model may be stored within a memory of external programmer 20, IMD 14 or another device.

In examples in which a clinician generates therapy programs for IMD 14 by selecting a stimulation field and subsequently generating the stimulation parameter values that may achieve the stimulation field, the volume of effect model may be an algorithmic model of the stimulation field selected by the clinician. For example, the volume of effect model may be an electrical field model that is generated based upon a patient anatomy data and a therapy program defining stimulation parameter values, where the volume of effect represents the areas of a patient anatomical region that will be covered by an electrical field during therapy delivery. The patient anatomy data may be specific to patient 12 or may represent data for more than one patient, e.g., model or averaged data of the anatomical structure and tissue conductivity of multiple patients. With respect to therapy system 10 of FIG. 1, the volume of effect model represents where electrical stimulation propagates through tissue from the electrodes carried by lead 16. Patient anatomy data may indicate one or more characteristics of patient tissue proximate to lead 16, and may be created from any type of imaging modality, such as, but not limited to, computed tomography (CT), magnetic resonance imaging (MRI), x-ray, fluoroscopy, and the like.

In other examples, an algorithmic model of the volume of effect may be generated after selecting a therapy program. For example, the clinician may select therapy parameter values that provide efficacious therapy to patient 12 and generate the therapy field resulting from the therapy parameter values with the aid of modeling software executing on a computing device, such as programmer 20 or a separate workstation or computing device. Again, the resulting volume of effect may be based on an algorithmic model that takes into consideration the therapy parameter values of the therapy program, the patient's anatomy, and the hardware characteristics of therapy system 10.

As another example, IMD 14 may deliver stimulation therapy to a volume of tissue of patient 12 and patient 12 or a clinician may provide feedback on the stimulation therapy using, for example, external programmer 20. In some instances, IMD 14 may deliver stimulation therapy at approximately the perception threshold stimulation intensity (which may have been determine previously, e.g., by delivering sub-threshold stimulation therapy and gradually increasing the stimulation intensity until patient 12 first perceives a substantial effect the stimulation). Patient 12 then may indicate an approximate volume of effect of the stimulation therapy using programmer 20 or another computing device. Patient 12 may provide the indication using a variety of input mechanisms, such as a touch screen, stylus, mouse, trackball, or the like. In some examples, patient 12 may select from among predefined anatomical regions (e.g., dermatomes) that approximately correspond to the volume of effect of the stimulation therapy. In other examples, external programmer 20 or another computing device may allow patient 12 to define a custom area or volume to represent the volume of effect of the stimulation therapy, e.g., by drawing, shading, outlining, or the like. The region selected or defined by patient 12 may then be used to represent the approximate volume of effect of the first stimulation therapy.

In other examples, the approximate volume of effect of the first stimulation therapy may be determined using extrapolation from volumes of effect of one or more supra-perception threshold stimulation therapies. For example, IMD 14 may be configured to deliver stimulation therapy at an intensity that is a predetermined amount greater than the perception threshold stimulation intensity, e.g., an intensity 25% greater than the perception threshold stimulation intensity. A user, such as a clinician or patient 12, may then indicate a volume of effect of the stimulation therapy using a computing device, such as external programmer 20. External programmer 20 may correlate the indicated volume of effect to the stimulation therapy program used to generate the stimulation therapy and save the correlated information, e.g., in a memory of external programmer 20.

IMD 14 then may be configured to deliver stimulation therapy at an intensity different than the previous intensity, but still above the perception threshold stimulation intensity, e.g., an intensity 15% greater than the perception threshold stimulation intensity. A user, such as a clinician or patient 12, may then indicate a volume of effect of the stimulation therapy using a computing device, such as external programmer 20. External programmer may correlate the indicated volume of effect to the stimulation therapy program used to generate the stimulation therapy and save the correlated information, e.g., in a memory of external programmer 20.

This process may be repeated for a predetermined number of supra-perception threshold stimulation intensities, e.g., at least two supra-perception threshold stimulation intensities. A computing device, such as external programmer 20, may then use the results (e.g., the indicated volumes of effect and the corresponding stimulation intensities) in a regression algorithm, e.g., a linear regression algorithm or nonlinear regression algorithm, to determine an equation that describes the correlation between the volume of effect and the stimulation intensity. The computing device, such as external programmer 20, may use this function to extrapolate an approximate volume of effect of the first stimulation therapy based on an inputted sub-perception threshold stimulation intensity, e.g., determine the approximate volume of effect of the first stimulation therapy based on the first stimulation intensity.

In some examples, the first stimulation therapy may be delivered in a regime at which supra-perception threshold stimulation therapy may be uncomfortable for some patients, e.g., patient 12. For SCS, some patients experience discomfort at some supra-perception threshold stimulation intensities when the stimulation therapy is delivered with a pulse frequency of less than about 20 hertz (Hz), or greater than about 200 Hz, or both. Such ranges (e.g., less than about 20 Hz and greater than about 200 Hz) may be referred to as uncomfortable stimulation regimes for SCS. However, stimulation therapy at these frequencies may provide therapeutic benefits to patient 12 in spite of the discomfort associated with the stimulation therapy. Thus, sub-perception threshold stimulation intensities may be used to substantially avoid discomfort of patient 12 while providing some therapeutic benefit to patient 12, e.g., some pain relief.

In some examples in which the first stimulation therapy is delivered at a pulse frequency of less than about 20 Hz, or greater than about 200 Hz, or both, the second stimulation therapy may be delivered at a similar pulse frequency but with an amplitude above the perception threshold intensity. The second stimulation therapy may be delivered by IMD 14 based on an instruction by the user (e.g., and provided to IMD 14 via programmer 20) to deliver the second stimulation therapy, and IMD 14 may deliver the second stimulation therapy temporarily. Thus, while patient 12 may experience some discomfort during delivery of the second stimulation therapy, the discomfort may be temporary. Additionally, in some implementations, IMD 14 may transition between the first stimulation therapy and the second stimulation therapy using a ramping profile, which may gradually increase the stimulation intensity. The gradual increase in stimulation intensity may reduce discomfort to patient 12 during the transition from the first stimulation therapy to the second stimulation therapy. Further, in some examples, programmer 20 is provided with a user interface element that allows patient 12 or another user to stop the transition from the first stimulation therapy to the second stimulation therapy, e.g., if patient 12 experiences excessive discomfort. In some instances, this may allow patient 12 or the clinician to determine that the first stimulation therapy is being delivered to a desired volume of tissue, that the perception threshold intensity has not changed, e.g., due to changes in tissue proximate to the electrodes carried by lead 16, or both.

In other examples, when the first stimulation therapy is delivered at a pulse frequency of less than about 20 Hz, or greater than about 200 Hz, or both, the second stimulation therapy may be delivered at a different pulse frequency, e.g., a pulse frequency between about 20 Hz and about 200 Hz. In some patients, SCS therapy at a pulse frequency between about 20 Hz and about 200 Hz is not uncomfortable for a range of intensities between the perception threshold stimulation intensity and a pain threshold intensity, which may be significantly greater than the perception threshold stimulation intensity. Hence, the range between about 20 Hz and about 200 Hz may be referred to as a comfortable stimulation regime for SCS. In these implementations, although the first and second stimulation therapies are delivered with different stimulation intensities and different stimulation frequencies, the stimulation parameter values for the first and second stimulation therapy programs may be selected so the volumes of effect of the first and second stimulation therapies are substantially equal. Because the volume of effect of the first stimulation therapy (the first volume of effect) and the volume of effect of the second stimulation therapy (the second volume of effect) are substantially the same (e.g., the same or nearly the same), use of the second stimulation therapy with a pulse frequency in a range that does not cause patient 12 discomfort may allow determination of the volume of tissue affected by the first stimulation therapy while not causing patient 12 discomfort.

In other examples, for SCS, IMD 14 is configured to deliver the first stimulation therapy at a pulse frequency of between about 20 Hz and about 200 Hz. IMD 14 may be configured to deliver the first stimulation therapy at a sub-perception threshold stimulation intensity, as described above. In some of these implementations, IMD 14 is configured to deliver the second stimulation therapy at a similar pulse frequency, but with an intensity that is greater than the sub-perception threshold stimulation intensity. In others of these implementations, IMD 14 is configured to deliver the second stimulation therapy at a different pulse frequency, and with an intensity that is greater than the sub-perception threshold stimulation intensity.

In other examples, for SCS, IMD 14 is configured to deliver the first stimulation therapy at a high pulse frequency. For example, IMD 14 may be configured to deliver the first stimulation therapy at a pulse frequency may be between about 1 KHz and about 100 KHz, such as between about 1 KHz and about 50 KHz, between about 3 KHz and about 15 KHz, or between about 8 KHz and about 10 KHz. In some examples, in which IMD 14 is configured to deliver the first stimulation therapy at the high pulse frequency, IMD 14 may be configured to deliver the second stimulation therapy at a lower frequency, e.g., between about 1 Hz and about 200 Hz, such as between about 1 Hz and about 100 Hz. Hence, IMD 14 may be configured to deliver the second stimulation therapy with a stimulation intensity above the perception threshold stimulation intensity patient 12 in either an uncomfortable regime (e.g., less than about 20 Hz for SCS) or a comfortable regime (e.g., between about 20 Hz and about 200 Hz for SCS).

In some examples, IMD 14 may be configured to generate and deliver the first simulation therapy chronically, e.g., substantially continuously for a period of time, such as days, weeks, months, or years. In other examples, IMD 14 may be configured to generate and deliver the first stimulation therapy intermittently, e.g., periodically or aperiodically at scheduled times or in response to an instruction received from a user, such as patient 12, via external programmer 20.

IMD 14 may not deliver the second stimulation therapy chronically, and may be configured to not deliver the second stimulation therapy unless IMD 14 receives an instruction to do so. For example, external programmer 20 may be configured with a user interface element that allows patient 12 or another user, such as a clinician, to request delivery of the second stimulation therapy by IMD 14. The user interface element may be, for example, a dedicated button, toggle switch, graphical user interface element selectable by the user, or the like. Upon receiving an input from the user via the user interface element, external programmer 20 may generate and transmit an instruction to IMD 14 to deliver the second stimulation therapy. In this way, the second stimulation therapy may be used by patient 12 or another user to determine a volume of tissue which the first stimulation therapy is affecting, even though patient 12 may not be able to substantially perceive the effect of the first stimulation therapy.

FIG. 2 is a conceptual diagram that illustrates another example therapy system 24 that may implement one or more aspects of this disclosure. The system in FIG. 2 includes IMD 14 configured to deliver peripheral nerve field stimulation (PNFS) therapy to patient 12. IMD 14 may be configured to deliver sub-perception threshold PNFS therapy and confirm a volume of effect of the sub-perception threshold PNFS therapy using any of the techniques described herein. IMD 14 may deliver PNFS via electrodes implanted in the region (e.g., region 26) where patient 12 experiences pain.

As described with respect to FIG. 1, IMD 14 may be configured to deliver a first stimulation therapy that is below a perception threshold intensity value. Because of this, patient 12 may not perceive a substantial effect of the first stimulation therapy. IMD 14 also may be configured to deliver a second stimulation therapy upon receiving an instruction from a user, such as patient 12 or a clinician, via external programmer 20. The second stimulation therapy may produce an intensity at or above a perception threshold stimulation intensity, such that patient 12 can perceive the effects of the second stimulation therapy, e.g., as a region of paresthesia. The volume of effect (e.g., the size and location) of the first stimulation therapy (the first volume of effect) may be mapped to the volume of effect (e.g., the size and location) of the second stimulation therapy (the second volume of effect, so the first volume of effect is substantially the same (e.g., the same or nearly the same) as the second volume of effect). In this way, patient 12 or another user may utilize temporary delivery of the second stimulation therapy to determine the first volume of effect.

Some example systems may include more than one IMD 14 for delivery of PNFS to one or more regions in which patient 14 experiences pain. In other examples, a single IMD 14 may deliver PNFS to one or more regions in which patient 12 experiences pain. In other examples, PNFS may be delivered in combination with other therapies, such as spinal cord stimulation (SCS), deep brain stimulation (DBS), cortical stimulation (CS), sacral nerve stimulation (SNS), drug therapy, and the like, as described in U.S. Patent Publication No. 2007/0073356 to Rooney et al., entitled, "COMBINATION THERAPY INCLUDING PERIPHERAL NERVE FIELD STIMULATION," which was filed on Jun. 9, 2006, and is incorporated herein by reference in its entirety.

In the example shown in FIG. 2, leads 18A and 18B deliver PNFS from IMD 14 to the tissue of patient 12 within a region 26 where patient 12 experiences pain. Leads 18A and/or 18B may be implanted within or between, for example, intradermal, deep dermal, or subcutaneous tissues of patient 12 at the region 26 where patient 12 experiences pain to deliver PNFS. These tissues may include skin and associated nerves and muscles and associated nerves or muscle fibers. In the illustrated example, region 26 is an axial region of the lower back of patient 12, but PNFS is not limited as such. Rather, leads 18A and 18B may be implanted in any region where patient 12 experiences pain. Leads 18A and/or 18B may deliver PNFS to one layer of tissue or multiple layers of a tissue as determined necessary by a clinician.

PNFS may ameliorate pain within the region of implantation by stimulating axons or small nerve fibers in the nearby dermal, subcutaneous, or muscular tissues, or the tissues themselves. The stimulation of these axons or fibers may cause orthodromic action potentials that propagate toward a spinal cord of patient 12, and modulate larger peripheral nerves (e.g., afferent nerves) and dorsal horn cells and/or synapses within the dermatomes that include the pain region, which may reduce pain experienced by patient 12 in that region. The stimulation of these axons or fibers may also cause antidromic action potentials that propagate toward the skin and modulate sympathetic outflow, which may reduce pain mediated by the sympathetic system, such as with some forms of complex regional pain syndrome.

Lead 18A or 18B may comprise, as examples, a substantially cylindrical lead with ring electrodes, a paddle lead, or a lead with a more complex, three-dimensional electrode array geometry, such as a cylindrical lead with electrodes disposed at various circumferential positions around the cylinder (e.g., with the aid of partial ring electrodes or segmented electrodes disposed at various circumferential positions around a lead having a generally round cross-section). In some examples, leads 18A or 18B may include electrodes, such as pad electrodes or segmented electrodes, on more than one surface. For example, leads 18A and 18B may be a paddle-type lead with electrodes on multiple surfaces, or a multiple level lead. In general, the disclosure may be used with a therapy system 10 including any type of lead, and is not limited to the leads described herein, or any particular type of implantable lead.

In some examples, IMD 14 may deliver stimulation therapy to region 26 in accordance with one or more stimulation therapy programs. In some implementations, adjusting the current or voltage amplitude and/or pulse width of a stimulation therapy program may change the stimulation intensity and/or volume in which patient 12 perceives paresthesia during delivery of electrical stimulation (e.g., for a supra-perception threshold stimulation intensity). The parameter values of a stimulation therapy program may be selected such that electrical stimulation reduces or eliminates the pain perceived by patient 12 within region 26. In other examples, IMD 14 may be configured to deliver electrical stimulation to multiple separate regions of patient 12.

The stimulation therapy program may include an electrode combination using one or more electrodes of one or both leads 18A and 18B. Each of leads 18A and 18B may be similar to lead 16 of FIG. 1. Electrode combinations used to provide PNFS therapy may be unipolar (e.g., one or more cathodes are provided by lead 18A or 18B and an anode is provided on the housing of IMD 14) or bipolar (e.g., both cathodes and anodes are provided on leads 18A and/or 18B). In other examples, IMD 14 may be coupled to a single lead or more than two leads. Similar to FIG. 1, external programmer 20 may communicate with and transmit stimulation therapy programs or other commands to IMD 14.

Similar to IMD 14 of FIG. 1, which is configured to generate and deliver SCS, IMD 14 of FIG. 2 may deliver a first stimulation therapy in accordance with a first therapy program that defines a first stimulation intensity that is lower than a perception threshold stimulation intensity. IMD 14 may be further configured to generate and deliver a second stimulation therapy in accordance with a second stimulation therapy program that defines a second stimulation intensity that is at or above the perception threshold stimulation intensity. As discussed above, the second stimulation therapy may be used by patient 12 or another user to determine a volume of tissue which the first stimulation therapy is affecting, even though patient 12 may not be able to substantially perceive the effect of the first stimulation therapy.

As described above, a first volume of effect may be determined for the first therapy program and a second volume of effect may be determined for the second therapy program. The first volume of effect may represent the volume of tissue in which the first stimulation therapy produces a therapeutic effect. The second volume of effect may represent the volume of tissue in which the second stimulation therapy is perceivable by patient 12, e.g., in which patient 12 perceives paresthesia. The stimulation parameter values of the first and second stimulation therapies may be selected so the first volume of effect is substantially the same (e.g., the same or nearly the same) as the second volume of effect (e.g., the location and size of the first and second volumes of effect within patient 12 may be substantially the same). The first and second volumes of effect may be determined theoretically, e.g., using one or more mathematical models, or experimentally, e.g., by delivering the first or second stimulation therapies and receiving indications from patient 12 or a clinician regarding the volume of effect perceived by patient 12.

In some examples, the first stimulation therapy may be delivered in a regime that would cause discomfort to patient 12 if the stimulation therapy were delivered at supra-perception threshold stimulation intensities. For example, for PNS or PNFS, some patients may experience discomfort at some supra-perception threshold intensities when the stimulation therapy is delivered with a pulse frequency of less than about 10 Hz. However, stimulation therapy at these frequencies may provide therapeutic benefits to patient 12 in spite of the discomfort associated with the stimulation therapy. Sub-perception threshold stimulation intensities may be used to substantially avoid discomfort of patient 12 while providing some therapeutic benefit to patient 12, e.g., some pain relief.

In some examples in which the first stimulation therapy is delivered at a pulse frequency of less than about 10 Hz, the second stimulation therapy may be delivered at a similar pulse frequency but with an amplitude that results in a stimulation intensity at or above the perception threshold intensity. The second stimulation therapy may be delivered by IMD 14 based on an instruction by the user to deliver the second stimulation therapy, and IMD 14 may deliver the second stimulation therapy temporarily. Thus, while patient 12 may experience some discomfort during delivery of the second stimulation therapy, the discomfort may be temporary. Additionally, in some implementations, IMD 14 may transition between the first stimulation therapy and the second stimulation therapy using a ramping profile, which may gradually increase the stimulation intensity. The gradual increase in stimulation intensity may reduce discomfort to patient 12 during the transition from the first stimulation therapy to the second stimulation therapy. Further, in some examples, programmer 20 is provided with a user interface element that allows patient 12 or another user to stop the transition from the first stimulation therapy to the second stimulation therapy, e.g., if patient 12 experiences excessive discomfort. In some instances, this may allow patient 12 or the clinician to determine that the first stimulation therapy is being delivered to a desired volume of tissue, that the perception threshold intensity has not changed, e.g., due to changes in tissue proximate to the electrodes carried by lead 16, or both.

In other examples, when the first stimulation therapy is delivered at a pulse frequency of less than about 10 Hz, the second stimulation therapy may be delivered at a different pulse frequency, e.g., a pulse frequency greater than about 10 Hz. In some patients, PNS or PNFS therapy at a pulse frequency greater than about 10 Hz is not uncomfortable for a range of intensities between the perception threshold stimulation intensity and a pain threshold intensity, which may be significantly greater than the perception threshold stimulation intensity.

In other implementations, for PNS or PNFS, IMD 14 is configured to deliver the first stimulation therapy at a pulse frequency of greater than about 10 Hz. Such a range may be referred to as a comfortable stimulation regime for PNS or PNFS. IMD 14 may be configured to deliver the first stimulation therapy at a sub-perception threshold stimulation intensity, as described above. In some of these implementations, IMD 14 is configured to deliver the second stimulation therapy at a similar pulse frequency, but with an intensity that is greater than the perception threshold stimulation intensity. In others of these implementations, IMD 14 is configured to deliver the second stimulation therapy at a different pulse frequency, and with an intensity that is greater than the perception threshold stimulation intensity.

In other examples, for PNS or PNFS, IMD 14 is configured to deliver the first stimulation therapy at a high pulse frequency. For example, IMD 14 may be configured to deliver the first stimulation therapy at a pulse frequency may be between about 1 KHz and about 100 KHz, such as between about 1 KHz and about 50 KHz, between about 3 KHz and about 15 KHz, or between about 8 KHz and about 10 KHz. In some examples, in which IMD 14 is configured to deliver the first stimulation therapy at the high pulse frequency, IMD 14 may be configured to deliver the second stimulation therapy at a lower frequency, e.g., between about 1 Hz and about 200 Hz, such as between about 1 Hz and about 100 Hz. Hence, IMD 14 may be configured to deliver the second stimulation therapy with a stimulation intensity above the perception threshold stimulation intensity patient 12 in either an uncomfortable regime (e.g., less than about 10 Hz for PNS or PNFS) or a comfortable regime (e.g., between about 10 Hz and about 200 Hz for PNS or PNFS).

Figure 3:
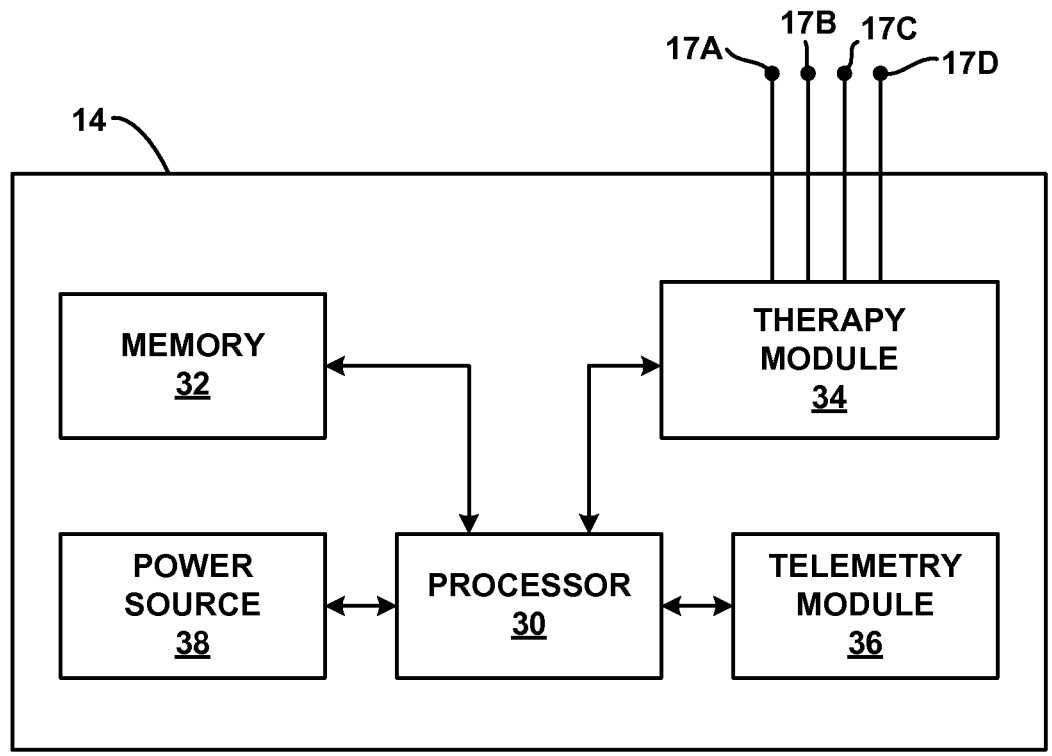
FIG. 3 is a functional block diagram illustrating an example IMD configured to deliver electrical stimulation therapy.

FIG. 3 is an example functional block diagram of the example IMD 14 shown in FIGS. 1 and 2. In the example of FIG. 3, IMD 14 includes processor 30, memory 32, therapy module 34, telemetry module 36, and power source 38. In other examples, IMD 14 may include a greater or fewer number of components. For example, IMD 14 may also include a sensing module configured to sense one or more physiological parameters of patient 12, an inductive coil to receive power from an external charging device, and a recharge module that manages recharging of power source 38.

In general, IMD 14 may comprise any suitable arrangement of hardware, alone or in combination with software and/or firmware, to perform the various techniques described herein attributed to IMD 14 and processor 30. In various examples, IMD 14 may include one or more processors 30, such as one or more microprocessors, digital signal processors (DSPs), application specific integrated circuits (ASICs), field programmable gate arrays (FPGAs), or any other equivalent integrated or discrete logic circuitry, as well as any combinations of such components. IMD 14 also, in various examples, may include a memory 32, such as random access memory (RAM), read only memory (ROM), programmable read only memory (PROM), erasable programmable read only memory (EPROM), electronically erasable programmable read only memory (EEPROM), flash memory, or other storage device, comprising executable instructions for causing the one or more processors to perform the actions attributed to them. Moreover, although processor 30, therapy module 34, and telemetry module 36 are described as separate modules, in some examples, processor 30, therapy module 34, and telemetry module 36 may be functionally integrated. In some examples, processor 30, therapy module 34, and telemetry module 36 may correspond to individual hardware units, such as ASICs, DSPs, FPGAs, or other hardware units.

Figure 4:
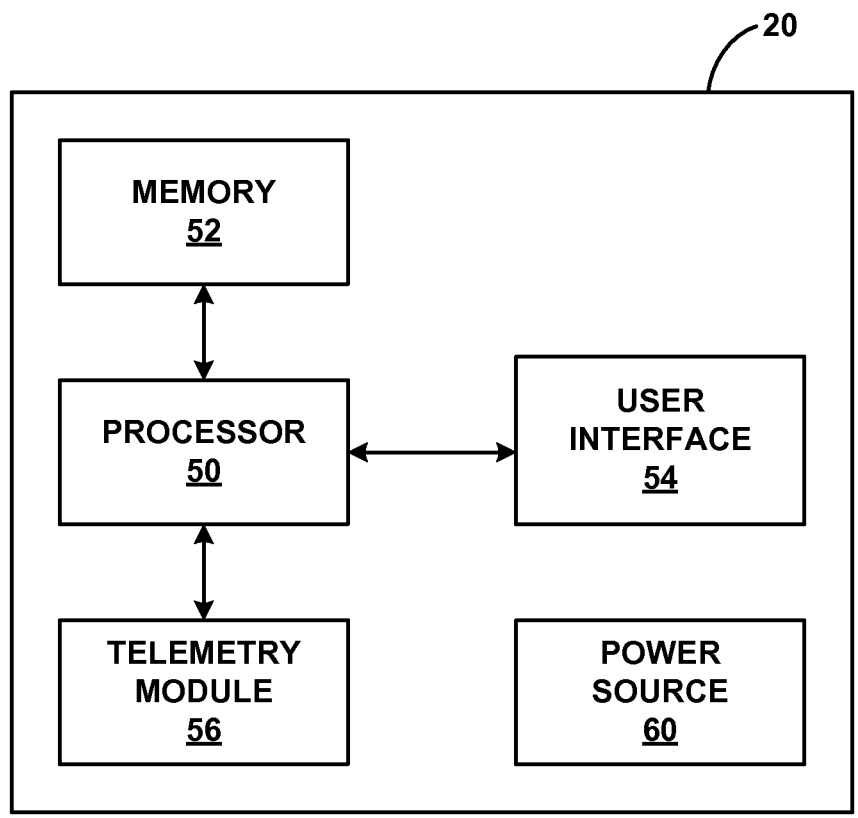
FIG. 4 is a functional block diagram illustrating an example external programmer.

Memory 32 may store therapy programs or other instructions that specify therapy parameter values for the therapy provided by therapy module 34 and IMD 14, including the first and second stimulation therapies. In some examples, memory 32 may also store instructions for communication between IMD 14 and programmer 20, or any other instructions required to perform tasks attributed to IMD 14. In some examples, memory 32 stores a duplicate of the data stored in memory 52 of external programmer 20 (FIG. 4).

Therapy module 34 is configured to generate and deliver electrical stimulation under the control of processor 30. In some examples, processor 30 controls therapy module 34 by accessing memory 32 to selectively access and load at least one of the stimulation therapy programs to therapy module 34. In such examples, relevant stimulation parameter values of the loaded therapy program may include a voltage amplitude, a current amplitude, a pulse frequency, a pulse width, a duty cycle, or the combination of electrodes 17A, 17B, 17C, and 17D (e.g., carried by lead 16 of FIG. 1 or leads 18A and 18B of FIG. 2) that therapy module 34 uses to deliver the electrical stimulation signal. In addition, processor 30 may access memory 32 to select a stimulation therapy program from a plurality of stimulation therapy programs stored in memory 32. Although therapy module 34 may be configured to generate and deliver electrical stimulation therapy via one or more of electrodes 17A, 17B, 17C, and 17D of lead 16, a different therapy module may be configured to provide different therapy to patient 12, such as drug delivery therapy via a catheter. These and other therapies may be provided by IMD 14.

An example range of electrical stimulation parameter values that may be used to deliver effective treatment for chronic pain, e.g., when applied in SCS to spinal cord 22 (FIG. 1), are listed below. While stimulation pulses are described, stimulation signals may be of any of a variety of forms such as sine waves or the like.

Pulse Frequency: between approximately 0.5 Hz and 10,000 Hz. In one example, pulse frequency may be between approximately 5 Hz and 250 Hz or between approximately 30 Hz and 130 Hz. In other examples, pulse frequency may be greater than 250 Hz or even greater than 1,000 Hz. Pulse frequencies greater than 1,000 Hz may be considered to be greater than the nerve firing potential of affected nerve fibers to inhibit nerve firing. For example, the pulse frequency may be between approximately 1,000 Hz and 10,000 Hz.

Amplitude: between approximately 0.1 volts and 50 volts, such as between approximately 0.5 volts and 20 volts, or between approximately 1 volt and 10 volts. In other embodiments, a current amplitude may be defined as the biological load in the voltage that is delivered. For example, the range of current amplitude may be between approximately 0.1 milliamps (mA) and 50 mA.

Pulse Width: between about 10 microseconds and 5000 microseconds. In some examples, the pulse width may be between approximately 100 microseconds and 1000 microseconds or between approximately 180 microseconds and 450 microseconds. With higher frequency pulses, the pulse width may be smaller to accommodate the increased frequency. For example, the pulse width may be between approximately 10 microseconds and 50 microseconds.

Memory 32 may store at least two stimulation therapy programs, e.g., at least a first stimulation therapy program and a second stimulation therapy program. Each of the therapy programs may specify one or more stimulation therapy parameter values, which may include, for example, an electrode configuration, a current or voltage amplitude, a pulse width, a pulse frequency (rate), a duty cycle, or the like. As described above, the first stimulation therapy program may define a stimulation intensity that is less than a perception threshold stimulation intensity of patient 12. The second stimulation therapy program may define a stimulation intensity that is greater than the perception threshold stimulation intensity. Also described above, the stimulation therapy delivered in accordance with the first stimulation therapy program (the first stimulation therapy) generates a first volume of effect and stimulation delivered in accordance with the second stimulation therapy program (the second stimulation therapy generates a second volume of effect. In some examples, the first volume of effect is substantially the same (e.g., the same or nearly the same) as the second volume of effect, e.g., the location and size of the first and second volumes of effect within patient 12 may be substantially the same. In other words, while the first and second stimulation therapy programs define different stimulation intensities, the stimulation therapy parameters of the first and second stimulation therapy programs may be selected so the first and second stimulation therapies produce substantially the same volumes of effect.

In some examples, memory 32 stores one or more ramping profiles that is retrieved and used by processor 30 to control therapy module 34 during transition between the first stimulation therapy program and the second stimulation therapy program (and/or during transition between the second stimulation therapy program and the first stimulation therapy program). The one or more ramping profiles may define, for example, a rate of change between the intensity of the first stimulation therapy program and the intensity of second stimulation therapy program. As described above, the change in stimulation intensity may be accomplished by changing one or more of the current or voltage amplitude, the pulse width, the duty cycle, or the like. Similarly, in examples in which the pulse frequencies of the first stimulation therapy program and the second stimulation therapy program are different, the one or more ramping profiles may define a rate of change between the pulse frequency of the first stimulation therapy program and the pulse frequency of the second stimulation therapy program.

In some examples, the intensity rate of change and/or the frequency rate of change may be substantially infinite, e.g., the change between the first intensity and the second intensity may be substantially instantaneous. In other examples, the intensity rate of change and/or the frequency rate of change may be finite, such that the intensity and/or frequency changes over a predetermined amount of time. In some instances, a gradual change in intensity and/or pulse frequency may reduce a chance that patient 12 experiences discomfort during the change from the first stimulation therapy to the second stimulation therapy. Additionally, a gradual change in intensity and/or pulse frequency may allow implementation of an override user input mechanism in external programmer 20. The override user input mechanism may allow patient 12 to interrupt the change to the second stimulation therapy program, e.g., if patient 12 experiences discomfort from the second stimulation therapy and wishes to stop the discomfort.

Similarly, memory 32 may store one or more ramping profile that processor 30 retrieves to control therapy module 34 during transition between the second stimulation therapy program and the first stimulation therapy program, e.g., upon completion of delivery of the second stimulation therapy. The one or more ramping profile may define a rate of decrease of stimulation intensity and/or a rate of change of stimulation frequency.

In some examples, in addition to being configured to generate and deliver the first and second stimulation therapies, therapy module 34 may be configured to generate and deliver a third stimulation therapy according to a third stimulation therapy program under the control of processor 30. In some examples, processor 30 controls therapy module 34 by accessing memory 32 to selectively access and load the third stimulation therapy program to therapy module 34. The third stimulation therapy program may include one or more stimulation therapy parameter values. In some examples, the third stimulation therapy defines an intensity and/or frequency regime that are different than the first stimulation therapy, and may be different than the second stimulation therapy.

For example, the third stimulation therapy may define a stimulation therapy within a comfortable frequency regime. As described above, the comfortable frequency regime may be between about 20 Hz and about 200 Hz for SCS or greater than about 10 Hz for PNS or PNFS. The third stimulation therapy may provide a different therapeutic effect than the first stimulation therapy. For example, the third stimulation therapy may provide paresthesia in the area in which patient 12 experiences pain (e.g., reduce hyperalgesia in the area in which patient 12 experiences pain).

In some examples, therapy module 34 may be configured to generate and deliver the third stimulation therapy chronically, e.g., for a period of days, months, or years. In some examples, therapy module 34 may be configured to generate and deliver the third stimulation therapy substantially continuously, while in other examples, therapy module 34 may be configured to generate and deliver the third stimulation therapy intermittently, e.g., in accordance with a schedule or in response to a command received from a user by processor 30 via telemetry module 36. In some instances, therapy module 34 may deliver the third stimulation therapy at substantially the same time as the first stimulation therapy, e.g., delivery of the first stimulation therapy and the third stimulation therapy may overlap in time. In other instances, therapy module 34 may deliver the third stimulation therapy at different times than the first stimulation therapy, e.g., therapy module 34 may alternate delivery of the first stimulation therapy and the third stimulation therapy.

IMD 14 may also include components to receive power from programmer 20 or a separate charging device to recharge a batter of power source 38. Power source 38 may include one or more capacitors, batteries, or other energy storage devices. IMD 14 may thus also include an inductive coil and a recharge module (both not shown) configured to manage the recharging session for power source 38. Although inductive coupling may be used to recharge power source 38, other wireless energy transfer techniques may alternatively be used. Alternatively, power source 38 may not be rechargeable.

Processor 30 may also control the exchange of information with programmer 20 and/or an external programmer using telemetry module 36. Telemetry module 36 may be configured for wireless communication using radio frequency protocols or inductive communication protocols. Telemetry module 36 may include one or more antennas configured to communicate with programmer 20, for example. Processor 30 may transmit operational information and receive therapy programs or therapy parameter adjustments via telemetry module 36. Also, in some examples, IMD 14 may communicate with other implanted devices, such as stimulators, control devices, or sensors, via telemetry module 36. For example, telemetry module 36 may receive user input, ramp schedules, or other commands from programmer 20.

FIG. 4 is an example functional block diagram of the example external programmer 20. While programmer 20 may generally be described as a hand-held device, programmer 20 may be a larger portable device or a more stationary device. In addition, in other examples, programmer 20 may be included as part of an external charging device or include the functionality of an external charging device. As illustrated in FIG. 4, programmer 20 may include a processor 50, memory 52, user interface 54, telemetry module 56, and power source 60. Memory 52 may store instructions that, when executed by processor 50, cause processor 50 and external programmer 20 to provide the functionality ascribed to external programmer 20 throughout this disclosure. For example, processor 50 may be configured to select a ramp schedule for increasing or decreasing a parameter value during delivery of electrical stimulation.

In general, programmer 20 comprises any suitable arrangement of hardware, alone or in combination with software and/or firmware, to perform the techniques attributed to programmer 20, and processor 50, user interface 54, and telemetry module 56 of programmer 20. In various examples, processor 50 may include one or more processors, such as one or more microprocessors, DSPs, ASICs, FPGAs, or any other equivalent integrated or discrete logic circuitry, as well as any combinations of such components. Programmer 20 also, in various examples, may include a memory 52, such as RAM, ROM, PROM, EPROM, EEPROM, flash memory, a hard disk, a CD-ROM, or other storage device, comprising executable instructions for causing the one or more processors to perform the actions attributed to them. Moreover, although processor 50 and telemetry module 56 are described as separate modules, in some examples, processor 50 and telemetry module 56 are functionally integrated. In some examples, processor 50 and telemetry module 56 correspond to individual hardware units, such as ASICs, DSPs, FPGAs, or other hardware units.

Telemetry module 56 may support wireless communication between IMD 14 and programmer 20 under the control of processor 50. Telemetry module 56 may also be configured to communicate with another computing device via wireless communication techniques, or direct communication through a wired connection. In some examples, telemetry module 56 may be substantially similar to telemetry module 36 of IMD 14 described herein, providing wireless communication via an RF or proximal inductive medium. In some examples, telemetry module 56 may include an antenna, which may take on a variety of forms, such as an internal or external antenna.

Examples of local wireless communication techniques that may be employed to facilitate communication between programmer 20 other computing devices include RF communication according to the 802.11 or Bluetooth specification sets or other standard or proprietary telemetry protocols. In this manner, other external devices may be capable of communicating with programmer 20 without needing to establish a secure wireless connection. As described herein, telemetry module 56 may be configured to transmit a ramp schedule or other stimulation parameter values to IMD 14 for delivery of stimulation therapy.

User interface 54 may include, for example, a user input mechanism (e.g., a button or keypad); lights; a speaker and microphone for transmitting and receiving voice commands; and a display, such as a liquid crystal (LCD), light-emitting diode (LED), or cathode ray tube (CRT). In some examples the display may be a presence-sensitive screen. User interface 54 may be configured to display any information related to the delivery of stimulation therapy, such as currently selected stimulation parameter values, ramping profiles, or any other therapy information. Processor 50 may also receive user input via user interface 54. The input may be, for example, in the form of pressing a button on a keypad or selecting an icon from a touch screen. The input may request starting or stopping electrical stimulation, the input may be a request for temporary delivery of the second stimulation therapy, or the input may request stopping transition to or delivery of the second stimulation therapy.

Memory 52 may store instructions that, when executed by processor 50, cause processor 50 and programmer 20 to provide the functionality ascribed to programmer 20 throughout this disclosure. For example, memory 52 may include instructions that cause processor 50 to obtain a first and/or second stimulation therapy program from memory 52, receive a user input and send a corresponding command to IMD 14, or instructions for any other functionality. In addition, memory 52 may include a plurality of stimulation therapy programs, where each stimulation therapy program includes a parameter set that defines stimulation therapy, and/or a plurality of ramping profiles. In some examples, programmer 30 may select a stimulation therapy program when a user, such as patient 12 or a clinician, provides input to start stimulation. In other examples, IMD 14 may request that programmer 30 selects a stimulation therapy program and transmit the stimulation therapy program, or at least one aspect of the stimulation therapy program, back to IMD 14 for delivery of corresponding electrical stimulation.

In some examples, memory 52 may store at least two stimulation therapy programs, e.g., at least a first stimulation therapy program and a second stimulation therapy program. As described above, the first stimulation therapy program may define a stimulation intensity below a perception threshold stimulation intensity and the second stimulation therapy program may define a stimulation intensity at or above the perception threshold stimulation intensity. The stimulation parameters of the first stimulation therapy program and the second stimulation therapy program may be selected so the first volume of effect of the first stimulation therapy program is substantially the same as the second volume of effect of the second stimulation therapy program, e.g., the location and size of the first and second volumes of effect within patient 12 may be substantially the same. In this way, as described above, the second stimulation therapy subsequently may be used to determine a volume of effect of the first stimulation therapy, e.g., by patient 12.

In some examples, the at least two stimulation therapy programs stored by memory 52 also may be stored in memory 32 of IMD 14. In other examples, the at least two stimulation therapy programs may not be stored in memory 32, and may be communicated from external programmer 20 to processor 30 of IMD 14 via telemetry modules 36 and 56 in response to a command from a user, e.g., via user interface 54, or in response to a request from processor 30 of IMD 14. In other examples, memory 52 may not store stimulation therapy programs, and memory 32 of IMD 14 (FIG. 3) may store the stimulation therapy programs.

In some examples, as described above, the intensity and/or pulse frequency may be changed gradually from that with which therapy module 34 delivers the first stimulation therapy to the intensity and/or pulse frequency with which therapy module 34 delivers the second stimulation therapy. In some instances, memory 52 may store one or more ramping profiles according to which processor 30 controls therapy module 34 to change from the stimulation parameter values of the first stimulation therapy program to the stimulation parameter values of the second stimulation therapy program. In other instances, memory 32 of IMD 14 (FIG. 3) may store the one or more ramping profiles and memory 52 may not store the one or more ramping profiles. Further details of the one or more ramping profiles are described above with respect to FIG. 3.

In some examples, user interface 54 includes a user interface element, e.g., a button, switch, toggle, or user interface element displayed by a presence-sensitive screen, that allows patient 12 or another user to cause processor 30 to control therapy module 34 to switch from the first stimulation therapy program to the second stimulation therapy program. When processor 50 receives the input from the user via user interface 54, processor 50 may generate and transmit an instruction to processor 30 of IMD 14 via telemetry module 56 of external programmer 20 and telemetry module 36 of IMD 14. In some examples, along with the instruction, processor 30 may transmit one or more stimulation parameter values of the second stimulation therapy program and/or one or more ramping profile. In response to receiving the instruction, processor 30 of IMD 14 controls therapy module 34 to transition from delivery the first stimulation therapy to the second stimulation therapy, e.g., transitioning using one or more ramping profile (which may be stored in memory 32 or memory 52).

In some examples, user interface 54 also includes an interrupt user interface element, which allows a user, such as patient 12 or a clinician, to interrupt, e.g., stop, the transition from the first stimulation therapy program to the second stimulation therapy program. The interrupt user interface element may include, for example, a button, switch, toggle, or user interface element displayed by a presence-sensitive screen. In response to receiving an input from the user, e.g., patient 12 or a clinician, via the interrupt user interface element, processor 50 may generate and transmit using telemetry module 56 an instruction to processor 30 to stop transitioning to or delivering stimulation therapy according to the second stimulation therapy program. In response, processor 30 may control therapy module 34 to cease delivery of all stimulation therapy or may control therapy module 34 to return to delivering stimulation therapy in accordance with the first stimulation therapy module. An interrupt user interface element may allow the user, such as patient 12, to stop the second stimulation therapy if the user no longer desires the second stimulation therapy, e.g., because the second stimulation therapy is causing discomfort.

Figure 5:
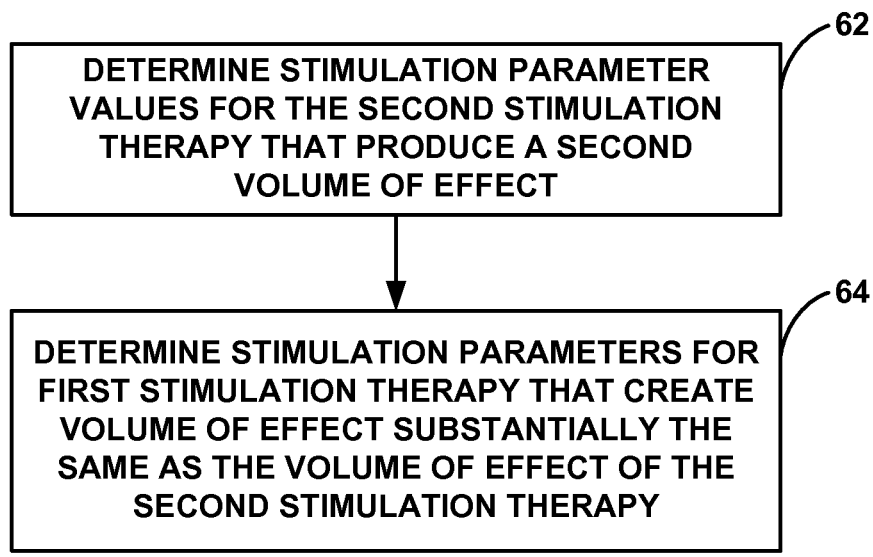
FIG. 5 is a flow diagram illustrating an example technique for determining stimulation parameter values for first and second stimulation therapy programs that define substantially equal volume of effects.

In some examples, external programmer 20 also may determine stimulation parameter values for the first and second stimulation therapy programs that result in substantially the same volumes of effect within patient 12. An example technique for determining stimulation parameter values for the first and second stimulation therapy programs that result in substantially the same volumes of effect is illustrated in FIG. 5. FIG. 5 will be described with reference to programmer 20 of FIG. 4 for purposes of illustration only. In other examples, another computing device may be used to determine stimulation parameter values for the first and second stimulation therapy programs. In some examples, processor 50 may implement the techniques illustrated in FIG. 5 automatically, e.g., without user intervention or control after initiating the technique. In other examples, processor 50 may implement the technique illustrated in FIG. 5 under control of a user, such as a clinician, who controls processor 50 via programmer 20. Additionally, although FIG. 5 illustrates step (62) as occurring before step (64), in other examples, step (64) may occur before step (62), e.g., the stimulation parameter values for the first stimulation therapy program and the first volume of effect may be determined before the stimulation parameter values for the second stimulation therapy program and the second volume of effect.

The technique illustrated in FIG. 5 includes determining, with processor 50, stimulation parameter values that produce a second volume of effect for the second stimulation therapy, e.g., the stimulation therapy delivered at an intensity greater than the perception threshold stimulation intensity (62). In some examples, as shown in FIG. 5, the stimulation parameter values for the second stimulation therapy and the volume of effect of the second stimulation therapy (the second volume of effect) may be determined first because the second stimulation therapy is perceptible to patient 12, e.g., is delivered at an intensity at or above the perception threshold stimulation therapy. In other examples, the stimulation parameter values and volume of effect for the first stimulation therapy (the first volume of effect) may be determined first, and the stimulation parameter values for the second stimulation therapy program and the second volume of effect may be determined second.

As described above, the second volume of effect may be determined theoretically, e.g., based on one or more mathematical models, or experimentally, e.g., based on therapy deliver and responses from patient 12 or another user. For example, processor 50 (or a processor of another computing device) may determine the second volume of effect using an algorithm that models the second volume of effect based on a stimulation therapy program, an anatomy of patient 12, and the hardware characteristics of therapy system 10.

In examples in which a clinician generates therapy programs for IMD 14 by selecting a stimulation field and subsequently generating the stimulation parameter values that may achieve the stimulation field, the second volume of effect model may be an algorithmic model of the stimulation field selected by the clinician. For example, the second volume of effect model may be an electrical field model that processor 50 generates based upon a patient anatomy data and a therapy program defining stimulation parameter values, where the volume of effect represents the areas of a patient anatomical region that will be covered by an electrical field during therapy delivery. The patient anatomy data may be specific to patient 12 or may represent data for more than one patient, e.g., model or averaged data of the anatomical structure and tissue conductivity of multiple patients. With respect to therapy system 10 of FIG. 1, the electrical field model represents where electrical stimulation propagates through tissue from the electrodes carried by lead 16. Patient anatomy data may indicate one or more characteristics of patient tissue proximate to lead 16, and may be created from any type of imaging modality, such as, but not limited to, computed tomography (CT), magnetic resonance imaging (MRI), x-ray, fluoroscopy, and the like.

In other examples, an algorithmic model of the volume of effect may be generated after selecting a therapy program. For example, the clinician may select therapy parameter values that provide efficacious therapy to patient 12 and generate the therapy field resulting from the therapy parameter values with the aid of modeling software executing on a computing device, such as programmer 20 or a separate workstation or computing device. Again, the resulting volume of effect may be based on an algorithmic model that takes into consideration the therapy parameter values of the therapy program, the patient's anatomy, and the hardware characteristics of therapy system 10. The volume of effect model may be stored within a memory of external programmer 20, IMD 14, or another device. Further details regarding determining a volume of effect using at least one mathematical model are described below with respect to FIG. 10.

As another example, processor 50 of programmer 20 may generate an instruction and transmit the instruction to processor 30 of IMD 14 using telemetry modules 56 and 36. The instruction may cause processor 30 to control therapy module 34 to deliver electrical stimulation therapy in accordance with the second stimulation therapy program. A user, such as patient 12 or a clinician, may then input a volume of effect of the second stimulation therapy using user interface 54.

FIGS. 6A-6D are schematic diagrams that illustrate example graphical user interface (GUI) screens 70a-70d that user interface 54 may display and which allow a user, such as patient 12 or a clinician, to input a volume of effect of the second stimulation therapy. GUI screens 70a-70d displaying body image templates 76, 82, 88 and 90, respectively, which correspond to four views of a body on screen 72.

In FIG. 6A, GUI screen 70a includes a front view template 76, a left view selection button 78, and a right view selection button 79. In FIG. 6B, GUI screen 70b includes a right view template 82, a front view selection button 84, and a back view selection button 85. In FIG. 6C, GUI screen 70c includes a back view template 88, the left view selection button 78, and the right view selection button 79. In FIG. 6D, GUI screen 70d includes a left view template 90, the front view selection button 84, and the back view selection button 85.

The various GUI screens 70a-70d allow the user to input a region indication 80 into external programmer 20 by drawing, shading, outlining, or otherwise indicating a region on the displayed template 76, 82, 88, 90, respectively, that corresponds to an affected volume of tissue (a volume of effect) of patient 12. After receiving indication 80, external programmer 20 may redisplay the template 76, 82, 88, 90 with shading to illustrate region indication 80 via display 72.

When the user, e.g., patient 12 or a clinician, is ready to view additional body templates, the user may select either a view button, e.g., the left view selection button 78 or right view selection button 79 from GUI screen 70a. Selecting left view selection button 78 causes external programmer 20 to display left view template 90, shown in FIG. 6D, and selecting right view selection button 79 causes external programmer 20 to display right view template 82, shown in FIG. 6B. Along with left or right view templates 90 and 82, external programmer displays any portion of region indication 80 that overlaps onto left or right view templates 90 and 82.

As shown in FIG. 6B, right view template 82 is displayed for external programmer 20 to accept region indications (not shown in FIG. 6B) from the user. The user may select front view selection button 84 or back view selection button 85 when ready to view additional body templates.

FIG. 6C illustrates back view template 88. Volume of effect indications may be entered by the user onto back view template 88 and then stored in the coordinate system. The user may choose to view either right view template 82 or left view template 90 via the body view selection buttons 78 and 79.

In FIG. 6D, left view template 90 is displayed along with a portion of volume of effect indication 80. As shown in FIG. 6A, volume of effect indication 80 is shaded to the left edge of front view template 76, so a portion of indication 80 overlaps onto left view template 90. The user may enter new region indications and/or add onto or modify volume of effect indication 80 on left view template 90. The user may then select front view selection button 84 or back view selection button 85 to redisplay previously displayed body views.

The user may switch between the four body view templates 76, 82, 88, and 90 via the body view selection buttons 78, 79, 84, and 85 as many times as necessary to indicate the volume of effect of the second stimulation therapy. Volume of effect indication 80 and, optionally, other volume of effect indications (not shown) may be manipulated, e.g., modified multiple times. Each change in the volume of effect indication 80 is illustrated on the redisplayed body templates 76, 82, 88 and 90.

In some examples, in addition to showing volume of effect indication 80, the GUI screens 70a-70d also may display an indication of a pain region of patient 12 on body templates 76, 82, 88, and 90. The pain region may be entered using GUI screens 70a-70d by a user, such as patient 12 or a clinician. The pain region may be manipulated, e.g., modified, multiple times to define the region in which patient 12 experiences pain. In some examples, this may facilitate selecting stimulation parameter values for the second stimulation therapy program that result in the second volume of effect covering substantially all of the pain region of patient 12.

In some instances, the initial stimulation parameter values for the second stimulation therapy program do not result in a second stimulation therapy that generates a second volume of effect that covers a predetermined region of the body of patient 12, e.g., the pain region of patient 12. As used herein, a stimulation therapy that "covers" a predetermined region of the body may least partially overlap the predetermined region, e.g., partially overlap, substantially overlap, or completely overlap the predetermined region. In some of these examples, processor 50, automatically or under control of a user, such as a clinician, may generate a new set of stimulation parameter values. The new set of stimulation parameter values may include at least one stimulation parameter value that is changed from the initial stimulation parameter values. Processor 50 then may generate an instruction and transmit the instruction to processor 30 of IMD 14 using telemetry module 56 and telemetry module 36 of IMD 14. The instruction may cause processor 30 to control therapy module 34 to deliver stimulation therapy in accordance with the new set of stimulation parameter values. The user, e.g., patient 12 or a clinician, then may enter the volume of effect of the new set of stimulation parameter values using, for example, GUI screens 70a-70d shown in FIGS. 6A-6D. If the new set of stimulation parameter values produces a volume of effect that covers the predetermined region of the body of patient 12, this set of stimulation parameter values may be used as the second stimulation therapy program. However, if the new set of stimulation parameter values does not produce a volume of effect that covers the predetermined region of the body of patient 12, this process may repeat until a set of stimulation parameter values produces a desired volume of effect. This set of stimulation parameter values then may be used as the second stimulation therapy program.

Once the second stimulation therapy program has been defined, processor 50 may proceed, automatically or under control of a user, to determine a set of stimulation parameter values for the first stimulation therapy program (64). The set of stimulation parameter values for the first stimulation therapy program may produce a stimulation intensity that is less than a perception threshold stimulation intensity and a volume of effect (a first volume of effect) that is substantially equal (e.g., equal or nearly equal) to the second volume of effect.

In some examples, as described with respect to the second volume of effect, processor 50 may determine the set of stimulation parameter values for the first stimulation therapy program and the first volume of effect theoretically, e.g., at least one mathematical model. For example, processor 50 may select a first set of stimulation parameter values and determine a volume of effect of the first set of stimulation parameter values using the volume of effect model described above. Processor 50 may compare the calculated volume of effect to the second volume of effect. If the calculated volume of effect is substantially the same (e.g., the same or nearly the same in both location and size) as the second volume of effect, processor 50 may define the first stimulation therapy program using the first set of stimulation parameter values. If the calculated volume of effect is not substantially the same as the second volume of effect, processor 50 may select a new set of stimulation parameter values, and calculate the volume of effect for the new set of stimulation parameter values using the neuron model and generated stimulation field model. Processor 50 may compare the calculated volume of effect for the new set of stimulation parameter values to the second volume of effect. If the calculated volume of effect is substantially the same (e.g., the same or nearly the same in both location and size) as the second volume of effect, processor 50 may define the first stimulation therapy program using this set of stimulation parameter values. If the calculated volume of effect is not substantially the same as the second volume of effect, processor 50 may continue to iterate this process until processor 50 determines a set of stimulation parameter values that produce a volume of effect that is substantially the same as the second volume of effect. Further details regarding determining a volume of effect using at least one mathematical model are described below with respect to FIG. 10.

Figure 7:
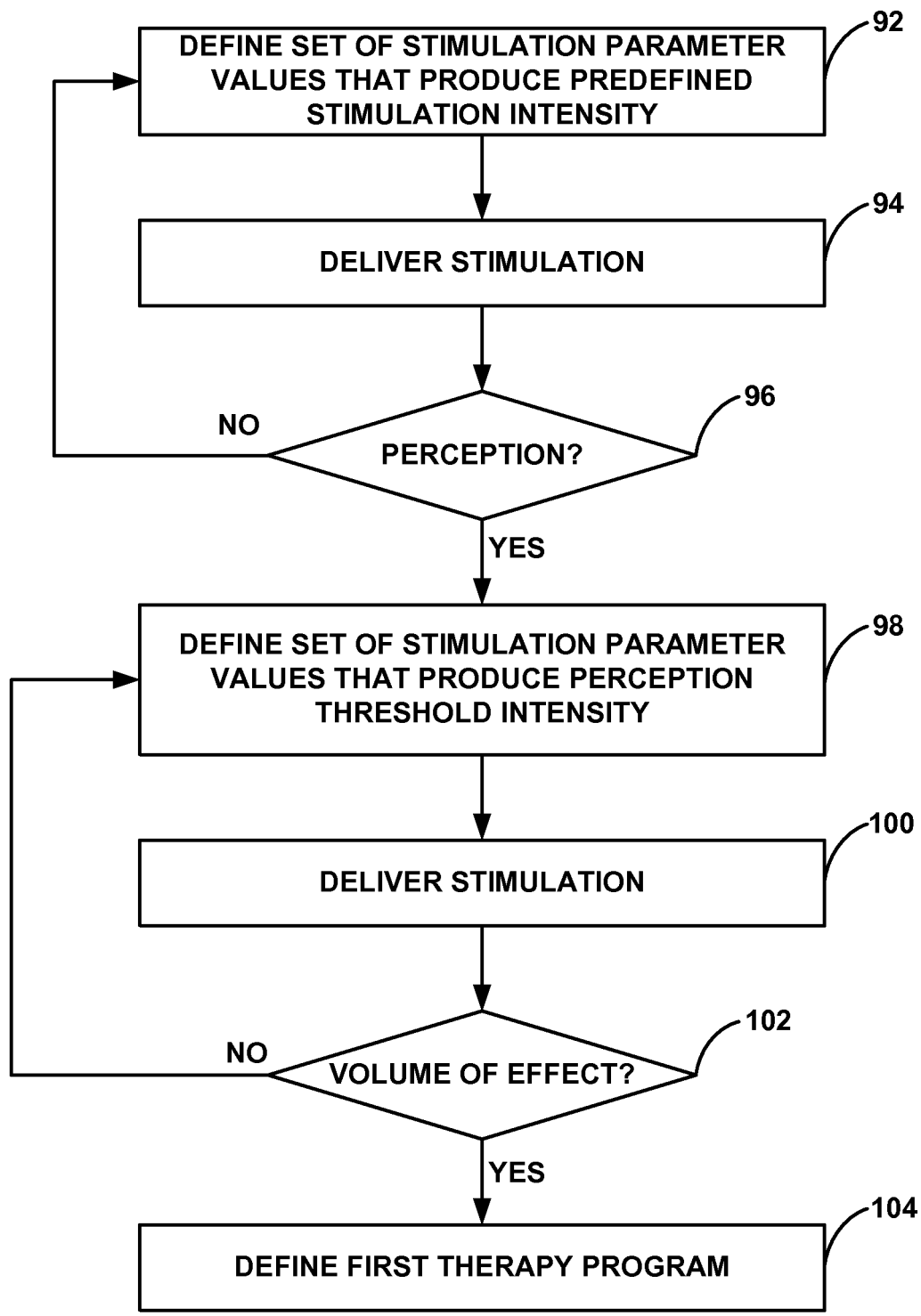
FIG. 7 is a flow diagram illustrating an example technique for defining a set of stimulation parameter values for a therapy program that defines a sub-perception threshold stimulation intensity.
Figure 8:
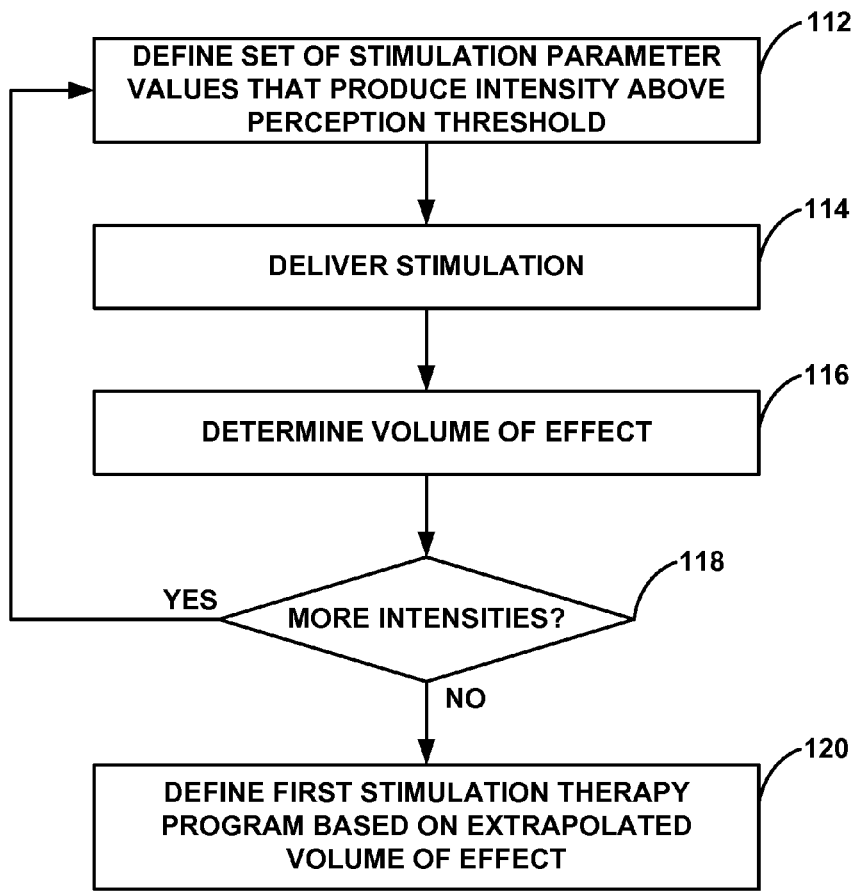
FIG. 8 is a flow diagram illustrating another example technique for defining a set of stimulation parameter values for a therapy program that defines a sub-perception threshold stimulation intensity.

In other examples, processor 50 may experimentally determine the first volume of effect and the set of stimulation parameter values for the first stimulation therapy program. FIGS. 7 and 8 are flow diagrams that illustrate two example techniques that processor 50 may implement to experimentally determine the first volume of effect and the set of stimulation parameter values for the first stimulation therapy program. In some examples, processor 50 may implement the techniques illustrated in FIGS. 7 and 8 automatically, e.g., without user intervention or control after initiating the technique. In other examples, control module 50 may implement the technique illustrated in FIGS. 7 and 8 under control of a user, such as a clinician, who controls processor 50 via programmer 20.

In the example of FIG. 7, processor 50 first may set stimulation parameter values such that the stimulation parameter values define a relatively low stimulation intensity, e.g., an intensity below an expected perception threshold intensity (92). These initial stimulation parameter value values may be selected by a clinician in some examples. In addition, in some examples, processor 50 generates an instruction and transmits the instruction to processor 30 of IMD 14 using telemetry modules 56 and 36. Based on the instruction, processor 30 controls therapy module 34 to deliver stimulation to patient 12 in the form of electrical pulses, and the stimulation parameter values include at least one of a voltage amplitude, a current amplitude, a pulse width, a pulse rate, or a duty cycle. In other examples, processor 30 and therapy delivery module 34 deliver stimulation to patient 12 in the form of an electrical waveform, and the stimulation parameter values include at least one of a voltage amplitude, a current amplitude, a frequency, a waveform shape, or a duty cycle.

In either case, processor 30 sets the stimulation parameter values to respective values to define a stimulation intensity, and controls therapy module 34 to delivery electrical stimulation to patient 12 according to the stimulation parameter values (94). During therapy delivery or after therapy module 34 delivers stimulation to patient 12, processor 50 monitors for an indication of that patient 12 perceived a substantial effect of the stimulation therapy (96). In some examples, such as when an electrode is implanted proximate to a spinal nerve or a muscle of patient 12, the threshold physiological response may include a flexing of a muscle of patient 12. In such examples, patient 12 or a clinician may observe the threshold physiological response and indicate a presence or absence of a physiological response to processor 50 via user interface 54 of programmer 20. In other examples, processor 50 may receive an indication that patient 12 perceived a substantial effect of the stimulation therapy, e.g., as paresthesia, via user interface 54 of programmer 20. The particular response that indicates that patient 12 perceived a substantial effect of the stimulation therapy may depend on the target tissue site. In this manner, a signal representing the user input from patient 12 may be related to the substantial effect of the stimulation therapy delivered to patient 12.

A perception threshold response may include, for example, an acute therapeutic response due to delivery of stimulation. For example, the threshold therapeutic response may include an acute (e.g., within about 30 seconds or less from initiation of stimulation delivery) perception of paresthesia.

When processor 50 does not receive a signal indicating a perception threshold response within a predetermined time period (e.g., within about five minutes, such as within about one minute) during or immediately after delivery of the stimulation according to the selected stimulation intensity ("NO" branch of block 96), e.g., via an input from a user, processor 50 may adjust at least one stimulation parameter value to increase a stimulation intensity of the stimulation signal (92). For example, processor 50 may increase a voltage amplitude or a current amplitude to increase the stimulation intensity. Processor 50 then generates an instruction and transmits the instruction to processor 30 that causes processor 30 to control therapy module 34 to deliver stimulation to patient 12 using the newly defined stimulation parameter values (94). Whether processor 50 determines whether the stimulation elicited a perception threshold response during or immediately after delivery of the stimulation according to the selected stimulation intensity may be based on the type of stimulation delivered and the type of perception threshold response that is expected.

Again, processor 50 monitors for a perception threshold response of patient 12 within a predetermined time period during or immediately after delivery of the stimulation according to the selected stimulation intensity (96). If processor 50 does not receive a signal indicating a perception threshold response ("NO" branch of block 96), processor 50 may again adjust at least one stimulation parameter value to increase a stimulation intensity of the stimulation signal (92). This process may repeat until processor 50 does receive a signal indicating a perception threshold response of patient 12 (96).

When processor 50 receives a signal that indicates a perception threshold response (e.g., via user interface 54) ("YES" branch of block 96), processor 50 may proceed to define a set of stimulation parameter values for the first therapy program that produces a predetermined volume of effect (98). In some examples, the predetermined volume of effect may be substantially the same as a previously-determined volume of effect of the second stimulation therapy. In other examples, the predetermined volume of effect may be substantially the same as a pain region defined by patient 12, e.g., via GUI screens 70*a*-70*d* shown in FIGS. 6A-6D.

In some examples, processor 50 may define the set of stimulation parameter values for the first therapy program based on input received from a user indicating a volume of effect of the set of stimulation parameter values. For example, as described above with respect to FIGS. 5 and 6A-6D, a user, such as patient 12 or a clinician, may input a volume of effect of a set of stimulation parameters using GUI screens 70*a*-70*d*. In some instances, the initial stimulation parameter values that result in the perception threshold stimulation intensity (determined in block 96 of FIG. 7) do not result in stimulation therapy that generates a second volume of effect that covers a predetermined region of the body of patient 12, e.g., the pain region of patient 12 and/or the volume of effect of the second stimulation therapy (the "NO" branch of block 102). In some of these examples, processor 50, automatically or under control of a user, such as a clinician, may generate a new set of stimulation parameter values that produce an intensity approximately equal to the perception threshold stimulation intensity and different volume of effect than the initial stimulation parameter values that result in the perception threshold stimulation intensity (98). The new set of stimulation parameter values may include at least one stimulation parameter value that is changed from the initial stimulation parameter values.

Processor 50 then may generate an instruction and transmit the instruction to processor 30 of IMD 14 using telemetry module 56 and telemetry module 36 of IMD 14. The instruction may cause processor 30 to control therapy module 34 to deliver stimulation therapy in accordance with the new set of stimulation parameter values (100). The user, e.g., patient 12 or a clinician, then may enter the volume of effect of the new set of stimulation parameter values using, for example, GUI screens 70*a*-70*d* shown in FIGS. 6A-6D. If the new set of stimulation parameter values produces the predetermined volume of effect, this set of stimulation parameter values may be used as the basis for the first stimulation therapy program (the "YES" branch of block 102). However, if the new set of stimulation parameter values does not produce the predetermined volume of effect (the "NO" branch of block 102), processor 50 may repeat this process until a set of stimulation parameter values produces the predetermined volume of effect, e.g., a volume of effect substantially the same as the second volume of effect and/or substantially the same as a pain region of patient 12. This set of stimulation parameter values then may be used as the basis for the first stimulation therapy program.

Once processor 50 determines the set of stimulation parameter values that is the basis for the first stimulation therapy program, processor 50 may change at least one of the stimulation parameter values to reduce a stimulation intensity below the perception threshold stimulation intensity while leaving the volume of effect of the set of stimulation parameter values substantially unchanged (e.g., unchanged or nearly unchanged) (104). For example, processor 50 may change at least one of an electrode configuration, current or voltage intensity, or pulse width in a manner that results in reducing the stimulation intensity while leaving the volume of effect substantially unchanged. In some examples, an amount that the volume of effect changes may be configured using at least one mathematical model, e.g., at least one of the mathematical models described herein as being used to theoretically determine a volume of effect of a stimulation therapy program. An example technique for adjusting the stimulation parameter values to reduce the intensity while leaving the volume of effect substantially unchanged is described with respect to FIG. 10. In some examples, the stimulation intensity of the first therapy program may be set to a predetermined percentage of the perception threshold stimulation intensity, e.g., 75%, 80%, 85%, or the like, of the perception threshold stimulation intensity. The first therapy program may be set to a predetermined percentage of the perception threshold stimulation intensity by, for example, modifying at least one stimulation parameter value to be the predetermined percentage of the stimulation parameter value that resulted in the perception threshold intensity.

FIG. 8 is flow diagram that illustrates another example technique for determining a first therapy program having a sub-perception threshold stimulation intensity and defining a first volume of effect. As described above, in some examples, processor 50 may implement the technique illustrated in FIG. 8 automatically, e.g., without user intervention or control after initiating the technique. In other examples, control module 50 may implement the technique illustrated in FIG. 8 under control of a user, such as a clinician, who controls processor 50 via programmer 20. Additionally, although the technique of FIG. 8 is described for purposes of illustration with reference to programmer 20 of FIG. 4, in other examples, other computing devices, e.g., IMD 14, may implement the technique illustrated in FIG. 8.

Although not shown in FIG. 8, in some examples, the technique may include determining a perception threshold stimulation intensity. As described with respect to FIG. 7, the perception threshold stimulation intensity may be determined by processor 50 by defining a set of stimulation parameter values that produce a stimulation intensity below an expected perception threshold stimulation intensity (92), causing IMD 14 to deliver stimulation therapy according to the set of stimulation parameter values (94), and receiving a signal indicating whether or not patient 12 perceived a substantial effect of the stimulation therapy (96). If patient 12 did not perceive a substantial effect of the stimulation therapy (the "NO" branch of block 96), processor 50 may define a new set of stimulation parameter values that are expected to produce a stimulation intensity greater than the previous set of stimulation parameter values (92), causing IMD 14 to deliver stimulation therapy according to the new set of stimulation parameter values (94), and receiving a signal indicating whether or not patient 12 perceived a substantial effect of the stimulation therapy (96). Processor 50 may repeat this process until processor 50 receives a signal indicating that patient 12 perceived a substantial effect of the stimulation therapy (the "YES" branch of block 96). Processor 50 then may implement the technique of FIG. 8. In other examples, the perception threshold stimulation intensity may be determined in other ways, such as using an average perception threshold stimulation intensity for a population of patients.

After a perception threshold is determined, the technique of FIG. 8 includes defining, with processor 50, a set of stimulation parameter values that produce a stimulation intensity above the perception threshold stimulation intensity (112). In some examples, the stimulation intensity may be a predetermined amount above the perception threshold stimulation intensity, e.g., a predetermined percentage above the perception threshold stimulation intensity. For example, processor 50 may increase at least one of a current or voltage amplitude, a pulse width, a duty cycle, or the like by a predetermined percentage above the perception threshold value of the at least one of the current or voltage amplitude, pulse width, duty cycle, or the like. In an example, processor 50 may increase the at least one of the current or voltage amplitude, pulse width, duty cycle, or the like by about 25%.

Processor 50 then may generate an instruction that includes the set of stimulation parameters values. Processor may transmit the instruction to processor 30 of IMD 14 using telemetry modules 56 and 36. The instruction also may cause processor 30 of IMD 14 to control therapy module 34 to deliver stimulation therapy using the set of stimulation parameter values (114). Once processor 30 of IMD 14 has controlled therapy module 34 to deliver therapy (114), processor 50 may receive a signal indicating a volume of effect of the stimulation therapy delivered according to the set of stimulation parameter values (116). In some examples, as described above with respect to FIGS. 5 and 6A-6D, patient 12 or another user may input the volume of effect using user interface 54 of programmer 20, e.g., by defining or selecting the volume of effect using an input device.

After receiving the signal indicating the volume of effect of the stimulation therapy delivered according to the set of stimulation parameters (116), processor 50 determines whether stimulation therapy is to be delivered at a different stimulation intensity above the perception threshold stimulation intensity (118). When processor 50 determines there are no more stimulation intensities at which therapy is to be delivered (the "NO" branch of block 118), processor 50 proceeds to define a first stimulation therapy program (120), as described below.

However, when processor determines that stimulation therapy is to be delivered at additional stimulation intensities, e.g., to collect more data points for use in the mathematical curve fitting algorithms used to determine the first therapy program, described below, (the "YES" branch of block 118), processor 50 defines a set of stimulation parameter values that produce a stimulation intensity above the perception threshold stimulation intensity (112). This set of stimulation parameter values may be selected to produce a stimulation intensity that is different than the stimulation intensity produced by the previous set of stimulation parameters. In some examples, the stimulation intensity may be a predetermined amount above the perception threshold stimulation intensity, e.g., a predetermined percentage above the perception threshold stimulation intensity. For example, processor 50 may increase at least one of a current or voltage amplitude, a pulse width, a duty cycle, or the like by a predetermined percentage above the perception threshold value of the at least one of the current or voltage amplitude, pulse width, duty cycle, or the like. In an example, processor 50 may increase the at least one of the current or voltage amplitude, pulse width, duty cycle, or the like by about 15%.

Processor 50 then may generate an instruction that includes the set of stimulation parameters values. Processor may transmit the instruction to processor 30 of IMD 14 using telemetry modules 56 and 36. The instruction also may cause processor 30 of IMD 14 to control therapy module 34 to deliver stimulation therapy using the set of stimulation parameter values (114). Once processor 30 of IMD 14 has controlled therapy module 34 to deliver therapy (114), processor 50 may receive a signal indicating a volume of effect of the stimulation therapy delivered according to the set of stimulation parameter values (116), as described above.

Processor 50 may continue this process of defining a set of stimulation parameter values (112), controlling (i.e., causing) therapy module 34 to deliver stimulation therapy according to the set of stimulation parameter values (114), and receiving signal indicating a volume of effect of the stimulation therapy delivered according to the set of stimulation parameter values (116) until determining that there are no more stimulation intensities at which stimulation therapy is to be delivered (the "NO" branch of block 118). For example, processor 50 may define at least three sets of stimulation parameters, which produce at least three different stimulation intensities at or above the perception threshold stimulation intensity.

Once processor 50 determines that there are no more stimulation intensities at which stimulation therapy is to be delivered (the "NO" branch of block 118), processor 50 may proceed to define a set of stimulation parameter values for use in the first therapy program using extrapolation (120). For example, based on the previously delivered stimulation therapies and the previously received volume of effect information for each of the previously delivered stimulation therapies, processor 50 may generate an equation that describes the relationship between stimulation intensity and volume of effect. Processor 50 may determine the equation using one or more mathematical curve fitting algorithms, such as a regression analysis (e.g., linear regression, nonlinear regression, or the like).

Processor 50 them may use the equation to extrapolate a set of stimulation parameter values that generate sub-perception threshold stimulation intensity and a predetermined volume of effect, e.g., a volume of effect equal to the second volume of effect or a pain region of patient 12. Processor 50 them may use this set of stimulation parameter values for the first stimulation therapy program (120).

Figure 9:
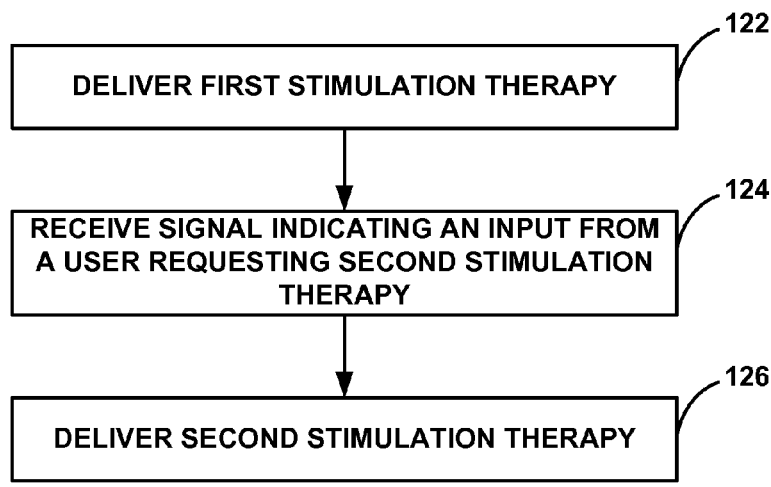
FIG. 9 is a flow diagram illustrating an example technique for delivering a stimulation therapy that defines an intensity at or above a perception threshold stimulation intensity in response to receiving an input from a user.

FIG. 9 is a flow diagram that illustrates a technique that may be implemented by a system, e.g., therapy system 10 of FIG. 1 or therapy system 24 of FIG. 2, to deliver stimulation therapy in accordance with a first stimulation therapy program and deliver a stimulation therapy in accordance with a second stimulation therapy program in response to an input received from a user, such as patient 12 or a clinician. The technique of FIG. 9 will be described with reference to therapy system 10 of FIG. 1 for purposes of illustration only, and may be implemented by other systems, e.g., therapy system 24 of FIG. 2.

As described above, the first stimulation therapy program may define a first volume of effect and a first stimulation intensity, which is less than a perception threshold stimulation intensity. Because of this, patient 12 may not substantially perceive delivery of the first stimulation therapy. The second stimulation therapy program may define a second volume of effect substantially equal to the first volume of effect. Additionally, the second stimulation therapy program defines a second intensity, which is greater than the perception threshold stimulation intensity. In this way delivery of stimulation in accordance with the second stimulation therapy program may allow a user, such as patient 12 or a clinician, to determine a volume of effect of the first stimulation therapy program based on the volume of effect of the second stimulation therapy program. This may be useful to allow patient 12 or the clinician to determine if the first volume of effect has moved relative to the desired location of the effect of the first stimulation therapy, e.g., a pain region of patient 12, or otherwise changed. The relative movement between the first volume of effect and the desired location may be due to, for example, displacement (e.g., migration) of a lead that carries electrodes used to deliver the first stimulation therapy, movement of the pain region of patient 12, or the like.

The technique of FIG. 9 includes delivering, with IMD 14, the first stimulation therapy (122). As described above, processor 30 of IMD 14 may control therapy module 34 of IMD 14 to generate the first stimulation therapy. The first stimulation therapy may be delivered to patient 12 via lead 16 (FIG. 1) and one or more of electrodes 17A-17D (FIG. 3). Therapy module 34 may generate the first stimulation therapy as a sequence of electrical pulses or a substantially continuous electrical signal. The first stimulation therapy may produce a stimulation intensity that is less than a perception threshold stimulation intensity and a first volume of effect.

In some examples, processor 30 controls therapy module 34 to deliver the first stimulation therapy chronically, e.g., for a period of days, months, or years. In other examples, processor 30 controls therapy module 34 for shorter periods of times, such as seconds, minutes, hours at a time, e.g., in response to command from a user, such as a clinician or patient 12, received via external programmer 20. Processor 30 may control therapy module 34 to deliver the first stimulation therapy substantially continuously, e.g., without times during which the first stimulation therapy is not delivered, or intermittently. When processor 30 controls therapy module 34 to deliver the first stimulation therapy intermittently, therapy module 34 may generate and deliver the first stimulation therapy periodically, e.g., according to a consistent schedule, or aperiodically, e.g., with different periods of time between delivery of the first stimulation therapy.

The technique of FIG. 9 also includes receiving, e.g., with processor 50 of external programmer 20, a signal indicating input from a user, such as patient 12 or a clinician, requesting delivery of the second stimulation therapy in accordance with the second stimulation therapy program (124). The input may be received via user interface 54 of external programmer 20, e.g., via a button, switch, or user interface element of a presence-sensitive screen, such as a touch screen. When processor 50 receives the signal indicating a command from a user to deliver the second stimulation therapy, processor 50 may generate an instruction and transmit the instruction to processor 30 of IMD 14 using telemetry module 56 of programmer 20 and telemetry module 36 of IMD 14. In some instances, the instruction instructs processor 30 to retrieve the second stimulation therapy program from memory 32, suspend delivery of the first stimulation therapy, and deliver electrical stimulation therapy according to the second stimulation therapy program. In other instances, the instruction includes the second stimulation therapy program and the instruction to suspend delivery of the first stimulation therapy and deliver stimulation therapy according to the second stimulation therapy program. In other examples, the input may be received by processor 30 of IMD 14, e.g., via a sensor in IMD 14 that senses a physical input from a user, such as tapping a location on patient 12 proximate to IMD 14.

In response to the instruction, processor 30 of IMD 14 controls therapy module 34 to generate and deliver the second stimulation therapy (126). Processor 30 may control therapy module 34 to generate and deliver the second stimulation therapy for a limited amount of time. For example, processor 30 may control therapy module 34 to generate and deliver the second stimulation therapy for a predetermined time, such as 30 seconds or one minute. As another example, processor 30 may control therapy module 34 to generate and deliver the second stimulation therapy until a signal is received by processor 30 indicating that a user, such as patient 12 or a clinician, wishes to stop delivery of the second stimulation therapy.

The second stimulation therapy program is configured to define a second volume of effect that is substantially equal to the first volume of effect and a second stimulation intensity, which is greater than the perception threshold stimulation intensity. In some examples, processor 30 may control therapy module 34 to transition from delivery of the first stimulation therapy to the second stimulation therapy using a ramping profile, which may gradually change an intensity of the stimulation therapy and/or a stimulation frequency of the stimulation therapy. The ramping profile may reduce a chance of discomfort for patient 12 during the transition between the first stimulation therapy and the second stimulation therapy. In some instances, processor 30 may control therapy module 34 to transition from the second stimulation therapy to the first stimulation therapy using a ramping profile, e.g., upon stopping delivery of the second stimulation therapy.

Once processor 30 has controlled therapy module 34 to deliver the second stimulation therapy, processor 50 may receive a signal represents an input from a user that indicates whether or not the second volume of effect still covers the desired tissue volume, e.g., a tissue volume in which patient 12 experiences pain. Because the first and second volumes of effect are substantially the same in size and location, whether the second volume of effect covers the desired tissue volume implies whether the first volume of effect covers the desired tissue volume.

For example, processor 50 may present using an element of user interface 54 (e.g., a display) a user interface screen to a user, such as patient 12 or a clinician, that requests the user to indicate using user interface 54 whether the second volume of effect covers the desired tissue volume. The user then may indicate whether the second volume of effect does or does not cover the desired tissue volume. In some instances, the user may further indicate using user interface 54, the extent to which the second volume of effect covers the desired tissue volume. For example, the user may select one or more descriptions provided by processor 50 using user interface 54 that describe the extent to which the second volume of effect covers the desired tissue volume (e.g., partially, substantially, fully, or the second volume of effect extends beyond the desired tissue volume). As another example, processor 50 may present one or more body image templates 76, 82, 88 and 90 (FIGS. 6A-6D) using a display and receive a signal indicating regions of the body image templates 76, 82, 88 and 90 that the user selects or defines to indicate the second volume of effect.

When processor 50 determines that the second volume of effect continues to cover the desired tissue volume, processor 50 may not change any stimulation parameter values of the first or second stimulation therapy programs. Processor 50 may generate and transmit an instruction to processor 30 using telemetry modules 36 and 56 to continue to control therapy module 34 to deliver electrical stimulation therapy according to the first stimulation therapy program.

In some examples, when the second volume of effect has changed relative to the desired tissue volume (e.g., moved, shrunk, or expanded), processor 50 may generate and transmit an alert to the user or another entity, e.g., using user interface 54 or telemetry module 56. For example, processor 50 may generate and transmit an alert to a computing device accessible to a clinician managing the therapy to inform the clinician that the second volume of effect has changed relative to the desired tissue volume. The user or the clinician then may schedule a time for clinician to modify therapy parameter values for the first and second therapies to produce volumes of effect that substantially or fully cover the desired tissue volume.

Figure 10:
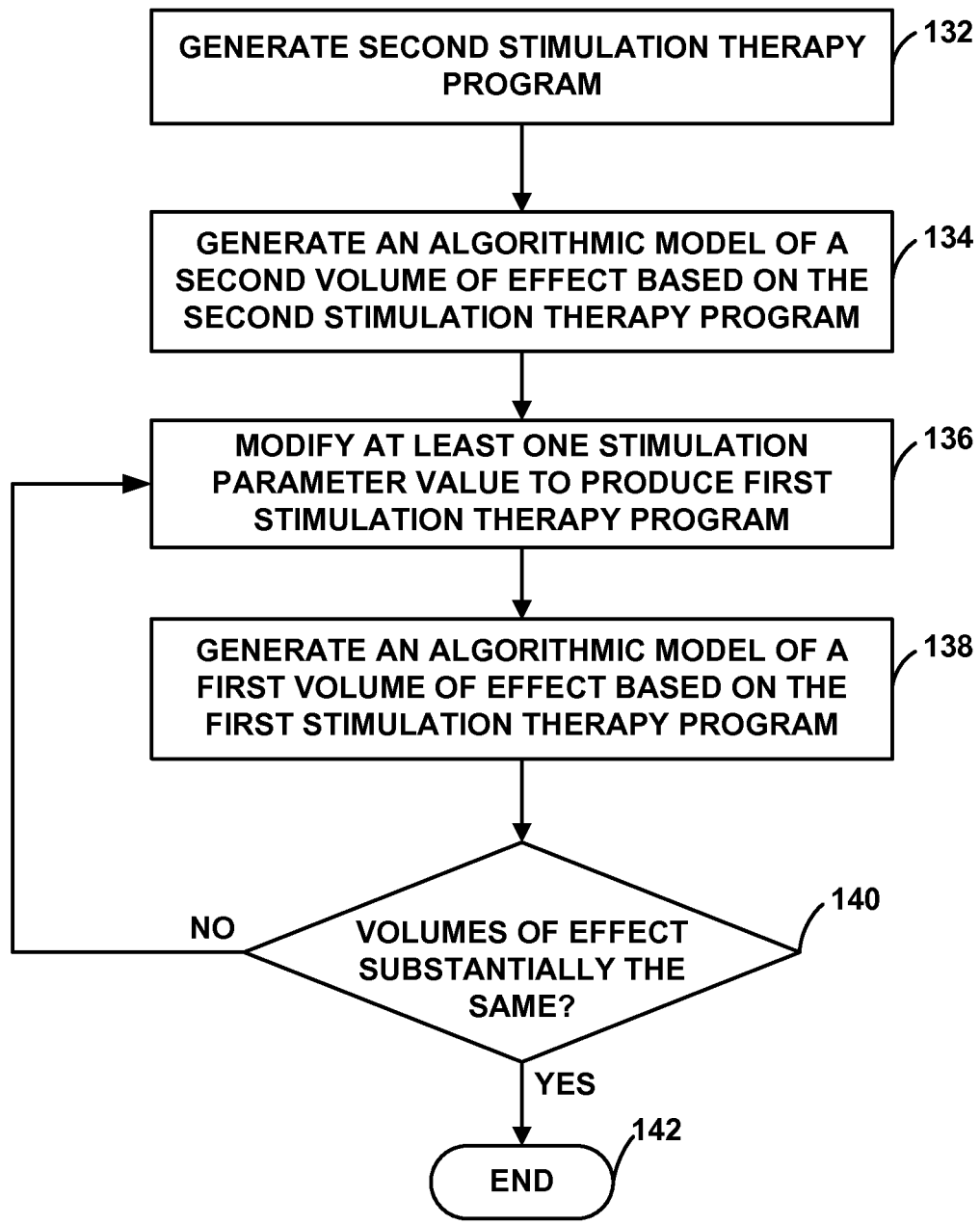
FIG. 10 is a flow diagram that illustrates an example technique for theoretically determining a volume of effect.

FIG. 10 is a flow diagram that illustrates an example technique for theoretically determining a volume of effect, e.g., of the first stimulation therapy, the second stimulation therapy, or both. While the flow diagram of FIG. 10 is described with respect to defining the first stimulation therapy program based on the second stimulation therapy program, in other examples, the technique of FIG. 10 may be used to define the second stimulation therapy program based on the first stimulation therapy program. The technique shown in FIG. 10 will be described with reference to therapy system 10 of FIG. 1, IMD 14 of FIG. 3, and external programmer 20 of FIG. 4 for purposes of illustration only. In other examples, the technique shown in FIG. 10 may be implemented at least in part by at least one processor of another computing device or devices.

As illustrated in FIG. 10, processor 50 generates a second stimulation therapy program (132). In some examples, processor 50 may facilitate evaluation of one or more therapy parameter values in order to generate the second stimulation therapy program. For example, memory 52 of programmer 20 may store an evaluation sequence that guides the user in the selection of electrode combinations and stimulation parameter values, or automatically selects electrode combinations and stimulation parameter values for evaluation of efficacy. For example, the evaluation sequence may specify a predetermined progression of electrode combinations to be selected for evaluation, or provide rules for dynamic selection of electrode combinations during the course of evaluation.

Memory 52 also may record efficacy information associated with one or more of the tested programs. Specifically, upon selection of an electrode combination and stimulation parameters as a program, processor 50 may direct processor 30 of IMD 14 to apply the program. Upon application of the program, patient 12 may provide feedback concerning efficacy. The user, which may be a clinician or the patient 12, then records the efficacy information in memory 52 of programmer 20, e.g., using user interface 54. In this manner, different stimulation therapy programs may be rated in terms of efficacy so that the user ultimately may select an effective electrode combination and stimulation parameters.

After determining the second stimulation therapy program for patient 12 (132), processor 50 may generate an algorithmic model of a second volume of effect for the second stimulation therapy program (134). The algorithmic model of the second volume of effect represents tissue in which patient 12 will perceive the second stimulation therapy when IMD 14 is delivering therapy to patient 12 according to the second stimulation therapy program.

The second volume of effect model may vary depending upon the stimulation parameter values of the second stimulation therapy program and the anatomy of patient 12 proximate to the target tissue site for the electrical stimulation therapy. For example, depending on the target tissue site for stimulation, an electrical field resulting from stimulation therapy delivered according to a particular therapy program may have a different stimulation area or a different centroid of stimulation. The algorithm implemented by processor 50 to generate the second volume of effect model, therefore, considers the therapy parameter values of the second stimulation therapy program, the anatomy of patient 12 proximate to the target stimulation site, and the hardware characteristics of therapy system 10.

Once processor 50 has generated the algorithmic model of the second volume of effect based on the second stimulation therapy program (134), processor 50 may change a value of at least one of the stimulation parameters to produce a first stimulation therapy program, which defines a stimulation intensity below a perception threshold stimulation intensity (136). For example, processor 50 may change a value of the amplitude (current or voltage), pulse width, duty cycle, or the like to reduce the stimulation intensity, while maintaining substantially constant volume of effect. As described above, the volume of effect of the first stimulation therapy may represent the volume of tissue in which the first stimulation therapy produces a therapeutic effect, even though patient 12 may not perceive the therapeutic effect.

Processor 50 then may generate an algorithmic model of the first volume of effect based on the first stimulation therapy program (138). The algorithmic model of the first volume of effect represents tissue in which the first stimulation therapy produces a therapeutic effect.

The first volume of effect model may vary depending upon the stimulation parameter values of the first stimulation therapy program and the anatomy of patient 12 proximate to the target tissue site for the electrical stimulation therapy. For example, depending on the target tissue site for stimulation, an electrical field resulting from stimulation therapy delivered according to a particular therapy program may have a different stimulation area or a different centroid of stimulation. The algorithm implemented by processor 50 to generate the first volume of effect model, therefore, considers the therapy parameter values of the first stimulation therapy program, the anatomy of patient 12 proximate to the target stimulation site, and the hardware characteristics of therapy system 10.

Processor 50 may compare the first volume of effect model to the second volume of effect model to determine if the first and second volumes of effect are substantially the same (140). In one example, processor 50 compares at least one characteristic of the first volume of effect model to a respective characteristic of the second volume of effect model. The one or more compared field characteristics may be selected based on the characteristics of the first volume of effect model that may affect the efficacy of the first stimulation therapy. In addition, the characteristics may be weighted based on their impact on the efficacy of the first stimulation therapy, and the comparison between the algorithmic models of the first volume of effect and the second volume of effect may be made on the weighted characteristics.

In the case of SCS delivered by therapy system 10 (FIG. 1), the centroid of stimulation may affect the efficacy of therapy more than the total volume of the electrical field or activation field. Thus, processor 50 may compare the centroid of stimulation of the first volume of effect model based on the first stimulation therapy program with the centroid of stimulation of the second volume of effect model based on the second stimulation therapy program in order to determine whether to modify the therapy program. Again, processor 50 may compare more than one field characteristics of the first volume of effect model with the second volume of effect model.

In some examples, processor 50 computes one or more metrics that indicate the similarity between the first volume of effect model with the second volume of effect model. As one example, processor 50 may determine the ratio of the first and second volume of effect models. Other metrics may include the percentage of overlap between the first and second volume of effect models, or the total volume of the first volume of effect model that does or does not overlap the second volume of effect model.

In some examples, processor 50 presents the first volume of effect model and the second volume of effect model on the display of user interface 54 of programmer 20. For example, the first and second volume of effect models may be overlaid on a representation of the target anatomical region of patient 12 for the therapy delivery (e.g., as shown in FIGS. 6A-6D). A user may visually or otherwise compare the displayed fields and provide feedback to processor 50 via user interface 54.

Based on the comparison between the first and second volume of effect models, processor 50 may adjust one or more therapy parameter values, e.g., respective values for the pulse width, frequency or amplitude defined by the first stimulation therapy program (136) (the "NO" branch of block 140). For example, if the first volume of effect is substantially larger than the second volume of effect, the clinician or another user of programmer 20 may adjust one or more stimulation parameter values to generate a smaller first volume of effect. Processor 50 may suggest a parameter adjustment to a user via user interface 54 or automatically adjust one or more stimulation parameter values based on the calculated metrics. Memory 52 of programmer 20 may include, for example, a set of therapy parameter value modification rules that enables processor 50 determine how the first volume of effect may be modified (e.g., decreased in volume). In some examples, processor 50 compares a metric indicative of the ratio between the first volume of effect and the second volume of effect to a threshold value and adjusts the first stimulation therapy program based on the comparison. Memory 52 may store the metric values determined by processor 50 based on the comparison between the first volume of effect and the second volume of effect, as well as any relevant threshold values and rules for stimulation therapy program modification.

In some examples, after processor 50 modifies the first stimulation therapy program, processor 50 generates an algorithmic model of the modified first volume of effect ("modified first volume of effect model") resulting from therapy delivery by therapy system 10 according to the modified first stimulation therapy program defining the adjusted set of stimulation parameter values (138). The algorithmic model of the modified first volume of effect may be generated using the same or a different algorithm that is used to generate the algorithmic model of the previous first volume of effect. In some examples, the modified first volume of effect model produced by the adjusted set of stimulation parameter values may more closely resemble the second volume of effect model. If the previous first volume of effect model based on the previous first stimulation therapy program had a volume substantially larger than the second volume of effect, the modified first volume of effect that is based on the modified therapy program may be have a smaller volume than the previous first volume of effect model, which may be closer to the second volume of effect.

After processor 50 modifies the first stimulation therapy program and generates an algorithmic model of the modified first volume of effect based on the modified first therapy program, processor 50 may compare the modified first volume of effect and the second volume of effect to determine if the first and second volumes of effect are substantially equal (140). If they are substantially equal (the "YES" branch of block 140), the technique ends (142) and the current stimulation parameters for the first and second stimulation therapy programs are used for the first and second stimulation programs. If they are not substantially the same (the "NO" branch of block 140), processor 50 may modify at least one stimulation parameter value to produce another modified first stimulation therapy program (136), generate an algorithmic model of another modified first volume of effect based on the modified first stimulation therapy (138), and compare the modified first volume of effect to the second volume of effect (140). This process may iterate until processor 50 determines, automatically or under control of a user, that the first volume of effect and the second volume of effect are substantially the same (e.g., in location and size). The process then may end (142), the current stimulation parameters for the first and second stimulation therapy programs are used for the first and second stimulation programs.

In one example, an implantable medical device (IMD) includes a therapy delivery module and a processor configured to control the therapy delivery module to deliver electrical stimulation therapy to a patient in accordance with a first stimulation therapy program, wherein the first stimulation therapy program defines a first stimulation intensity below a perception threshold stimulation intensity of the patient, and wherein the first stimulation therapy produces a first volume of effect within the patient, receive a signal indicating an instruction from a user to switch therapy delivery from the first stimulation therapy program to a second stimulation therapy program, wherein the second stimulation therapy program defines a second stimulation intensity at or above the perception threshold stimulation intensity, and wherein the second stimulation therapy produces a second volume of effect within the patient that is substantially the same as the first volume of effect, and, in response to reception of the signal, controls the therapy delivery module to deliver electrical stimulation therapy to the patient in accordance with the second stimulation therapy program to confirm the first volume of effect of the first stimulation therapy program.

In some examples, the first stimulation therapy program includes a first pulse frequency and the second stimulation therapy program includes a second pulse frequency different than the first pulse frequency. In some examples, the electrical stimulation therapy includes spinal cord stimulation therapy, wherein the first pulse frequency includes a frequency of less than about 20 hertz (Hz), and wherein the second pulse frequency includes a frequency of between about 20 Hz and about 200 Hz. In some examples, the electrical stimulation therapy includes spinal cord stimulation therapy, wherein the first pulse frequency includes a frequency greater than about 200 hertz (Hz), and wherein the second pulse frequency includes a frequency of between about 20 Hz and about 200 Hz. In some examples, the electrical stimulation therapy includes peripheral nerve stimulation, wherein the first pulse frequency includes a frequency less than about 10 hertz (Hz), and wherein the second pulse frequency includes a frequency between about 10 Hz and about 60 Hz. In other examples, the processor is configured to control the therapy module to gradually transition from the first stimulation therapy program to the second stimulation therapy program based on a ramping profile.

In another examples, a method includes delivering, by a therapy delivery module, electrical stimulation therapy to a patient in accordance with the first stimulation therapy program, wherein the first stimulation therapy program defines a first stimulation intensity below a perception threshold stimulation intensity of the patient, and wherein the first stimulation therapy produces a first volume of effect within the patient. The method also includes receiving, by a processor, a signal indicating an instruction from a user to switch therapy delivery from the first stimulation therapy program to a second stimulation therapy program, wherein the second stimulation therapy program defines a second stimulation intensity at or above the perception threshold stimulation intensity, and wherein the second stimulation therapy produces a second volume of effect within the patient that is substantially the same as the first volume of effect and in response to receiving the signal, delivering, by the therapy delivery module, electrical stimulation therapy to the patient in accordance with the second stimulation therapy program to confirm the first volume of effect of the first stimulation therapy program.

In some examples, the first stimulation therapy program includes a first pulse frequency, wherein the second stimulation therapy program includes a second pulse frequency different than the first pulse frequency. In some examples, the stimulation therapy includes spinal cord stimulation therapy, wherein the first pulse frequency includes a frequency of less than about 20 hertz (Hz), and wherein the second pulse frequency includes a frequency of between about 20 Hz and about 200 Hz. In some examples, the stimulation therapy includes spinal cord stimulation therapy, wherein the first pulse frequency includes a frequency greater than about 200 hertz (Hz), and wherein the second pulse frequency includes a frequency of between about 20 Hz and about 200 Hz. In some examples, the stimulation therapy includes peripheral nerve stimulation, wherein the first pulse frequency includes a frequency less than about 10 hertz (Hz), and wherein the second pulse frequency includes a frequency between about 10 Hz and about 60 Hz. In other examples, the method includes gradually transitioning, with the therapy delivery module, from the first stimulation therapy program to the second stimulation therapy program based on a ramping profile.

In another example, a system includes means for delivering electrical stimulation therapy to a patient in accordance with the first stimulation therapy program, wherein the first stimulation therapy program defines a first stimulation intensity below a perception threshold stimulation intensity, and wherein the first stimulation therapy produces a first volume of effect within the patient, and means for receiving a signal indicating an instruction from a user to switch therapy delivery from the first stimulation therapy program to a second stimulation therapy program, wherein the second stimulation therapy program defines a second stimulation intensity at or above the perception threshold stimulation intensity, and wherein the second stimulation therapy produces a second volume of effect within the patient that is substantially the same as the first volume of effect. The system also includes means for, in response to receiving the signal, delivering electrical stimulation therapy to the patient in accordance with the second stimulation therapy program to confirm the first volume of effect of the first stimulation therapy program. In some examples, the first stimulation therapy program includes a first pulse frequency, and wherein the second stimulation therapy program includes a second pulse frequency different than the first pulse frequency.

In another example, a computer-readable storage medium comprises instructions that, when executed by at least one processor, cause the at least one processor to control a therapy delivery module to deliver electrical stimulation therapy to a patient in accordance with the first stimulation therapy program, wherein the first stimulation therapy program defines a first stimulation intensity below a perception threshold stimulation intensity, and wherein the first stimulation therapy produces a first volume of effect within the patient. The instructions, when executed by the at least one processor, also cause the at least one processor to receive a signal indicating an instruction from a user to switch therapy delivery from the first stimulation therapy program to a second stimulation therapy program, wherein the second stimulation therapy program defines a second stimulation intensity at or above the perception threshold stimulation intensity, and wherein the second stimulation therapy produces a second volume of effect within the patient that is substantially the same as the first volume of effect and, in response to the signal, control the therapy delivery module to deliver electrical stimulation therapy to the patient in accordance with the second stimulation therapy program to confirm the first volume of effect of the first stimulation therapy program. In some examples, the first stimulation therapy program includes a first pulse frequency, and wherein the second stimulation therapy program includes a second pulse frequency different than the first pulse frequency.

Techniques described herein may be implemented, at least in part, in hardware, software, firmware, or any combination thereof. For example, various aspects of the described embodiments may be implemented within one or more processors, including one or more microprocessors, digital signal processors (DSPs), application specific integrated circuits (ASICs), field programmable gate arrays (FPGAs), or any other equivalent integrated or discrete logic circuitry, as well as any combinations of such components. The term "processor" or "processing circuitry" may generally refer to any of the foregoing logic circuitry, alone or in combination with other logic circuitry, or any other equivalent circuitry. A control unit including hardware may also perform one or more of techniques of this disclosure.

Such hardware, software, and firmware may be implemented within the same device or within separate devices to support the various techniques described herein. In addition, any of the described units, modules or components may be implemented together or separately as discrete but interoperable logic devices. Depiction of different features as modules or units is intended to highlight different functional aspects and does not necessarily imply that such modules or units are realized by separate hardware, firmware, or software components. Rather, functionality associated with one or more modules or units may be performed by separate hardware, firmware, or software components, or integrated within common or separate hardware, firmware, or software components.

Techniques described herein may also be embodied or encoded in an article of manufacture including a computer-readable storage medium encoded with instructions. Instructions embedded or encoded in an article of manufacture including an encoded computer-readable storage medium may cause one or more programmable processors, or other processors, to implement one or more of the techniques described herein, such as when instructions included or encoded in the computer-readable storage medium are executed by the one or more processors. Computer readable storage media can include random access memory (RAM), read only memory (ROM), programmable read only memory (PROM), erasable programmable read only memory (EPROM), electronically erasable programmable read only memory (EEPROM), flash memory, a hard disk, a compact disc ROM (CD-ROM), a floppy disk, a cassette, magnetic media, optical media, or other computer readable storage media. In general, a computer-readable storage medium may be any tangible medium, such as one or more storage devices, that can contain or store a program for use by or in connection with an instruction execution system, apparatus, or device. Additional examples of computer-readable medium include computer-readable storage devices, computer-readable memory, and tangible computer-readable medium. In some examples, an article of manufacture may comprise one or more computer-readable storage media.

In some examples, computer-readable storage media may comprise non-transitory media. The term "non-transitory" may indicate that the storage medium is tangible and is not embodied in a carrier wave or a propagated signal. In certain examples, a non-transitory storage medium may store data that can, over time, change (e.g., in RAM or cache).

Various examples have been described. These and other examples are within the scope of the following claims.

What is claimed is:

1. A system comprising:
a therapy delivery module configured to:
deliver, via one or more electrodes of a plurality of implantable electrodes, electrical stimulation therapy to a tissue of a patient in accordance with a first stimulation therapy program, wherein the first stimulation therapy program defines a first stimulation intensity below a perception threshold stimulation intensity of the patient; and
deliver, via one or more electrodes of the plurality of implantable electrodes, stimulation therapy to the tissue of the patient in accordance with a second stimulation therapy program, wherein the second stimulation therapy program defines a second stimulation intensity at or above the perception threshold stimulation intensity; and
a processor configured to:
determine stimulation parameter values for the second stimulation therapy program that result in a second volume of effect within the patient; and
determine stimulation parameter values for the first stimulation therapy program that result in a first volume of effect within the patient that is substantially the same as the second volume of effect, wherein the first volume of effect represents a first volume of tissue in which a therapeutic effect is produced, and wherein the second volume of effect represents a second volume of tissue in which stimulation therapy is perceivable by the patient.

2. The system of claim 1, wherein the processor is configured to determine, using a neuron model and a generated stimulation field model, the stimulation parameter values for at least one of the first stimulation therapy program or the second stimulation therapy program.

3. The system of claim 2, wherein the processor is configured to determine, using the neuron model and the generated stimulation field model, at least one of the first volume of effect and the second volume of effect.

4. The system of claim 1, wherein the processor is configured to determine the stimulation parameter values for at least one of the first stimulation therapy program and the second stimulation therapy program by controlling the therapy module to deliver electrical stimulation therapy in accordance with a set of stimulation parameter values and receiving a signal representing an input from a user related to a third volume of effect of the stimulation therapy delivered by the therapy module in accordance with the set of stimulation parameter values.

5. The system of claim 1, wherein the processor is configured to determine at least one of the first volume of effect and the second volume of effect.

6. The system of claim 5, wherein the processor is configured to determine the first volume of effect by controlling the therapy module to deliver electrical stimulation therapy at a third stimulation intensity substantially equal to the perception threshold stimulation intensity and receiving a signal representing an input from a user related to a third volume of effect of the stimulation therapy delivered at the third stimulation intensity.

7. The system of claim 1, wherein the processor is configured to determine the stimulation parameter values of the first stimulation therapy program by:
controlling the therapy module to deliver electrical stimulation therapy at a third stimulation intensity at or above the perception threshold stimulation intensity;
receiving a first signal representing an input from a user related to a third volume of effect of the stimulation therapy delivered at the third stimulation intensity;
controlling the therapy module to deliver electrical stimulation therapy at a fourth stimulation intensity at or above the perception threshold stimulation intensity;
receiving a second signal representing an input from the user related to a fourth volume of effect of the stimulation therapy delivered at the fourth stimulation intensity;
controlling the therapy module to deliver electrical stimulation therapy at a fifth stimulation intensity at or above the perception threshold stimulation intensity;
receiving a third signal representing an input from the user related to a fifth volume of effect of the stimulation therapy delivered at the fifth stimulation intensity;
determining an equation describing a correlation between stimulation intensity and volume of effect based on the first, second, and third signals and the third, fourth, and fifth stimulation intensities; and
determining, using the equation describing the correlation between stimulation intensity and volume of effect, the stimulation parameter values for the first stimulation therapy program.

8. The system of claim 7, wherein the processor is configured to determine, using the equation describing the correlation between stimulation intensity and volume of effect, the first volume of effect.

9. The system of claim 1, wherein the first stimulation therapy program comprises a first pulse frequency, and wherein the second stimulation therapy program comprises a second pulse frequency different than the first pulse frequency.

10. The system of claim 1, further comprising an implantable medical device that comprises the therapy delivery module and the processor.

11. The system of claim 1, further comprising:
an implantable medical device that comprises the therapy delivery module; and
an external programmer that comprises the processor.

12. A method comprising:
delivering, by a therapy delivery module and via one or more electrodes of a plurality of implantable electrodes, electrical stimulation therapy to a tissue of a patient in accordance with a first stimulation therapy program, wherein the first stimulation therapy program defines a first stimulation intensity below a perception threshold stimulation intensity of the patient;
delivering, by the therapy delivery module and via one or more electrodes of the plurality of implantable electrodes, electrical stimulation therapy to the tissue of the patient in accordance with a second stimulation therapy program, wherein the second stimulation therapy program defines a second stimulation intensity at or above the perception threshold stimulation intensity;
determining, by a processor, stimulation parameter values for the second stimulation therapy program that result in a second volume of effect within the patient; and
determining, by the processor, stimulation parameter values for the first stimulation therapy program that result in a first volume of effect within the patient that is substantially the same as the second volume of effect, wherein the first volume of effect represents a first volume of tissue in which a therapeutic effect is produced, and wherein the second volume of effect represents a second volume of tissue in which stimulation therapy is perceivable by the patient.

13. The method of claim 12, wherein at least one of determining stimulation parameter values for the first stimulation therapy program and determining stimulation parameter values for the second stimulation therapy program comprises determining, using a neuron model and a generated stimulation field model, the stimulation parameter values for the respective stimulation therapy program.

14. The method of claim 13, further comprising determining, using the neuron model and the generated stimulation field model, at least one of the first volume of effect or the second volume of effect.

15. The method of claim 12, wherein at least one of determining stimulation parameter values for the first stimulation therapy program and determining stimulation parameter values for the second stimulation therapy program comprises:
delivering, by the therapy module, stimulation therapy in accordance with a set of stimulation parameter values; and
receiving a signal representing an input from a user related to a third volume of effect of the stimulation therapy delivered by the therapy module in accordance with a set of stimulation parameter values.

16. The method of claim 12, further comprising determining, by the processor, at least one of the first volume of effect or the second volume of effect.

17. The method of claim 16, wherein determining at least one of the first volume of effect of the second volume of effect comprises:
delivering, by the therapy module, stimulation therapy at a third stimulation intensity substantially equal to the perception threshold stimulation intensity; and
receiving a signal representing an input from a user related to a third volume of effect of the stimulation therapy delivered at the third stimulation intensity; and
using, by the processor, the volume of effect of the stimulation therapy delivered at the third stimulation intensity as the first volume of effect.

18. The method of claim 12, wherein determining the stimulation parameter values of the first stimulation therapy program comprises:
delivering, by the therapy module, electrical stimulation therapy at a third stimulation intensity at or above the perception threshold stimulation intensity;
receiving, by the processor, a first signal representing an input from a user related to a third volume of effect of the stimulation therapy delivered at the third stimulation intensity;
delivering, by the therapy module, electrical stimulation therapy at a fourth stimulation intensity at or above the perception threshold stimulation intensity;
receiving, by the processor, a second signal representing an input from the user related to a fourth volume of effect of the stimulation therapy delivered at the fourth stimulation intensity;
delivering, by the therapy module, electrical stimulation therapy at a fifth stimulation intensity at or above the perception threshold stimulation intensity;
receiving, by the processor, a third signal representing an input from the user related to a fifth volume of effect of the stimulation therapy delivered at the fifth stimulation intensity;
determining, by the processor, an equation describing the correlation between stimulation intensity and volume of effect based on the first, second, and third signals and the third, fourth, and fifth stimulation intensities; and
determining, by the processor and using the equation describing the correlation between stimulation intensity and volume of effect, the stimulation parameter values for the first stimulation therapy program.

19. The method of claim 18, further comprising determining, by the processor and using the equation describing the correlation between stimulation intensity and volume of effect, the first volume of effect.

20. The method of claim 12, wherein the first stimulation therapy program comprises a first pulse frequency, and wherein the second stimulation therapy program comprises a second pulse frequency different than the first pulse frequency.

21. The method of claim 12, wherein an implantable medical device comprises the therapy delivery module and the processor.

22. The method of claim 12, wherein an implantable medical device comprises the therapy delivery module and an external programmer comprises the processor.

23. A system comprising:
means for delivering, via one or more electrodes of a plurality of implantable electrodes, electrical stimulation therapy to a tissue of a patient in accordance with a first stimulation therapy program, wherein the first stimulation therapy program defines a first stimulation intensity below a perception threshold stimulation intensity of the patient;
means for delivering, via one or more electrodes of the plurality of implantable electrodes, electrical stimulation therapy to the tissue of the patient in accordance with a second stimulation therapy program, wherein the second stimulation therapy program defines a second stimulation intensity at or above the perception threshold stimulation intensity;

means for determining stimulation parameter values for the second stimulation therapy program that result in a second volume of effect within the patient; and means for determining stimulation parameter values for the first stimulation therapy program that result in a first volume of effect within the patient that is substantially the same as the second volume of effect, wherein the first volume of effect represents a first volume of tissue in which a therapeutic effect is produced, and wherein the second volume of effect represents a second volume of tissue in which stimulation therapy is perceivable by the patient.

24. The system of claim 23, further comprising:

means for determining the first volume of effect; and means for determining the second volume of effect.

25. A non-transitory computer-readable storage medium comprising instructions that, when executed by at least one processor, cause the at least one processor to:

control a therapy delivery module to deliver, via one or more electrodes of a plurality of implantable electrodes, electrical stimulation therapy to a tissue of a patient in accordance with a first stimulation therapy program, wherein the first stimulation therapy program defines a first stimulation intensity below a perception threshold stimulation intensity of the patient;

control the therapy delivery module to deliver, via one or more electrodes of the plurality of implantable electrodes, electrical stimulation therapy to the tissue of the patient in accordance with a second stimulation therapy program, wherein the second stimulation therapy program defines a second stimulation intensity at or above the perception threshold stimulation intensity;

determine stimulation parameter values for the second stimulation therapy program that result in a second volume of effect within the patient; and determine stimulation parameter values for the first stimulation therapy program that result in a first volume of effect within the patient that is substantially the same as the second volume of effect, wherein the first volume of effect represents a first volume of tissue in which a therapeutic effect is produced, and wherein the second volume of effect represents a second volume of tissue in which stimulation therapy is perceivable by the patient.

26. The non-transitory computer-readable storage medium of claim 25, further comprising instructions that cause the at least one processor to:

determine the first volume of effect; and determine the second volume of effect.

\* \* \* \* \*